(12) United States Patent
Lacey et al.

(10) Patent No.: US 6,538,180 B1
(45) Date of Patent: Mar. 25, 2003

(54) METHOD FOR INCREASING SUCROSE CONTENT OF PLANTS

(75) Inventors: Colin N. Lacey, Cambridge (GB); Stephen G. Hughes, Saffron Walden (GB); Christopher J. Harrison, Norwich (GB); Trevor L. Wang, Norwich (GB); Clifford L. Hedley, Norwich (GB)

(73) Assignee: Unilever Patent Holdings B.V., Vlaardingen (NL)

( * ) Notice: Subject to any disclaimer, the term of this patent is extended or adjusted under 35 U.S.C. 154(b) by 0 days.

(21) Appl. No.: 09/214,619

(22) PCT Filed: Jul. 3, 1997

(86) PCT No.: PCT/EP97/03613

§ 371 (c)(1),
(2), (4) Date: Jul. 15, 1999

(87) PCT Pub. No.: WO98/01574

PCT Pub. Date: Jan. 15, 1998

Related U.S. Application Data

(60) Provisional application No. 60/021,410, filed on Jul. 9, 1996.

(30) Foreign Application Priority Data

Jul. 18, 1996 (GB) ............................................. 9615103
Feb. 10, 1997 (GB) ............................................. 9702653

(51) Int. Cl.$^7$ .................... C12N 15/05; C12N 15/09; C12N 15/29; C12N 15/82; A01H 5/00

(52) U.S. Cl. ..................... 800/284; 800/278; 800/286; 800/295; 800/298; 435/69.1; 435/320.1; 435/468; 435/419; 536/23.1; 536/23.2; 536/23.6; 536/24.5

(58) Field of Search ................................ 800/284, 286, 800/295, 298, 278; 435/69.1, 320.1, 468, 419; 536/23.1, 23.2, 23.6, 24.5

(56) References Cited

U.S. PATENT DOCUMENTS 5,498,831 A * 3/1996 Burgess et al. ............. 800/205
6,127,605 A   10/2000 Webster ...................... 800/298

FOREIGN PATENT DOCUMENTS

| WO | 94/11520 | 5/1994 | |
| WO | WO 99/29161 | 6/1999 | ............ A01H/5/00 |

OTHER PUBLICATIONS

Lazar et al, "Transforming Growth Factor x: Mutation of Aspartic Acid 47 and Leucine 48 Results in Different Biological Activities", Mar. 1988, Molecular and Cellular Biology vol. 8 No. 3, pp. 1247–1252.*

Napoli, "Introduction of a Chimeric Chalcone Sunthase Gene into Petunia Results in Reversible Co–suppression of Homologous Genes in trans", Apr. 1990, The Plant Cell, vol. 2, pp. 279–289.*

Broun et al, "Catalytic Plasticity of Fatty Acid Modification Enzymes Underlaying Chemical Diversity of Plant Lipids", Nov. 1999, Science vol. 282, pp. 1315–1317.*

Penger et al. Plant Physiology, vol. 105, pp. 1439–1440, 1994.*

Bird et al. Biotechnology and Gen. Eng. Review, vol. 9, pp. 207–227, Dec. 1991.*

Sandler et al. Plant Mol. Biol. vol. 11, pp. 301–310, 1988.*

Smith et al. Nature, vol. 334, pp. 724–726, Aug. 1988.*

Kossmann et al. Progress in BioTech–10, Proceed. Int. Cont, pp. 271–278, Apr. 1995.*

Schulze et al, Plant, Cell and Environment, 17:795–809 (1994).

Hanson, Perspectives in Biochemical and Genetic Regulation of Photosynthesis, pp. 69–84 (1990).

Caspar et al, Plant Physiol., 79:11–17 (1985).

Hanson, et al, Plant Physiol., 88:838–844 (1988).

Huber et al, Plant Physiol., 99:1449–1454 (1992).

Hanson, Plant Physiol., 99:276–283 (1992).

Sicher et al, Physiologia Plantarium, 88:446–452 (1992).

Neuhaus et al, Planta, 182:445–454 (1990.

Bhattacharyya, M. et al "The Importance of Starch Biosynthesis in the Wrinkled Seed Shape Character of Peas Studied by Mendel " Plant Molecular Biology, vol. 22, 1993, pp. 525–531, XP002045358 Abstract + p. 526, Left Column.

Smith, A.M. et al "Evidence That the rb Locus Alters the Starch Content of Developing Pea Embrys Through an Effect on ADP Glucose Pyrophosphorylase" Plant Physiology, vol. 89, Sep. 15, 1988, pp. 1279–1284, XP002045359 cited in the application, pp. 1279, Left column, p. 1283; Table 2.

Hylton, C. et al, "The rb Mutation of Peas Causes Structural and Regulatory Changes in ADP Glucose Pyrophosporylase From Developing Embryos" Plant Physiology, vol. 99, 1992, pp. 1626–1634, XP002045360 p. 1626, Left Column.

(List continued on next page.)

*Primary Examiner*—Elizabeth F. McElwain
*Assistant Examiner*—Medina A. Ibrahim
(74) *Attorney, Agent, or Firm*—Morgan, Lewis & Bockius LLP

(57) ABSTRACT

Pea seeds, produced from peas of the rug3rug3 genotype, substantially lacking plastidial phosphoglucomutase activity which have higher sucrose levels at the end of the vining period and may be vined over and extended period compared to conventional vining varieties are provided. Polynucleootides encoding pea plastidial phosphoglucomutase useful for altering the sucrose and starch content of plants, particularly peas, are also disclosed.

6 Claims, 11 Drawing Sheets

OTHER PUBLICATIONS

Newman, T. et al "Genes Galore: A Summary of Methods for Accessing Results From Large–Scale Partial Sequencing of Anonymous Arabidopsis cDNA Clones" EMBL Sequence Data Library, Apr. 19, 1996, Hedleberg, Germany, XP002045361 Accession No. N967760.

Whitehouse, D.B. et al "Phosphoglucomutase 1: Complete Human and Rabbit mRNA Sequences and Direct Mapping of This Highly Polymorphic Marker on Human Chromosome 1" EMBL Sequence Data Library, Feb. 3, 1992, Heidelberg, Germany, XP002045362 Accession No. M83088.

Smith, A.M. et al: "What Controls the Amount and Structure of Starch in Storage Organs" Plant Physiology, vol. 107, 1995, pp. 673–677, XP002045363 See figure 1.

Muller–Rober, B et al "Approaches to Influence Starch Quantity and Starch Quality in Transgenic Plants" Plant, Cell and Environment, vol. 17, 1994 p. 601–613 XP002005943.

Wang. T.L. et al: "Seed Development in Peas: Knowing Your Three "r"s (or four, or five)" Seed Science Research, vol. 1, 1991, pp. 3–14, XP002045365.

Grevsen, K. and Kidmose, U.: "Yield, Plant Growth and Quality of Vining Pea Varieties at Early and Late Showing Dates" Tidsskr, Planteavl., vol. 96, 1992, pp, 279–292, XP002045366.

Bailey–Serres, J.: Unpublished EMBL Sequence Data Library, Mar. 13, 1997, Heidelberg, Germany, XP002045367 Accession No. U89342.

* cited by examiner

Fig. 1A

| | |
|---|---:|
| CAAACACATA GTTAAACAAA AAACACTCTC TCTTGACTCT TCGAAGAAAA AGTTGTCACT | 60 |

| | | | | | | | | | | | | | | | | |
|---|---|---|---|---|---|---|---|---|---|---|---|---|---|---|---|---:|
| GTTACAGACT CGATCA | ATG | GTC | TTC | TGT | TAC | AGA | CTC | GAC | AAC | TTC | ATC | | | | | 109 |
| | Met | Ala | Phe | Cys | Tyr | Arg | Leu | Asp | Asn | Phe | Ile | | | | | |
| | 1 | | | 5 | | | | | | 10 | | | | | | |
| ATC | TCT | GCG | TTT | AAA | CCC | AAA | CAC | TCA | AAT | GTC | CCA | CTT | TCA | ATT | CAT | 157 |
| Ile | Ser | Ala | Phe | Lys | Pro | Lys | His | Ser | Asn | Val | Pro | Leu | Ser | Ile | His | |
| | | | 15 | | | | | 20 | | | | | 25 | | | |
| CAT | TCA | TCA | TCC | AAT | TTT | CCT | TCT | TTC | AAA | GTT | CAA | AAC | TTT | CCT | TTC | 205 |
| His | Ser | Ser | Ser | Asn | Phe | Pro | Ser | Phe | Lys | Val | Gln | Asn | Phe | Pro | Phe | |
| | | 30 | | | | | 35 | | | | | 40 | | | | |
| AGG | GTT | CGC | TAT | AAT | TCA | GCT | ATT | AGA | GCC | ACT | TCA | TCT | TCC | TCT | TCT | 253 |
| Arg | Val | Arg | Tyr | Asn | Ser | Ala | Ile | Arg | Ala | Thr | Ser | Ser | Ser | Ser | Ser | |
| | 45 | | | | 50 | | | | | 55 | | | | | | |
| ACT | CCC | ACA | ACC | ATT | GCA | GAA | CCT | AAT | GAC | ATT | AAG | ATT | AAC | TCT | ATT | 301 |
| Thr | Pro | Thr | Thr | Ile | Ala | Glu | Pro | Asn | Asp | Ile | Lys | Ile | Asn | Ser | Ile | |
| 60 | | | | 65 | | | | | 70 | | | | | 75 | | |
| CCT | ACT | AAA | CCT | ATT | GAA | GGA | CAA | AAA | ACT | GGT | ACC | AGT | GGT | CTA | AGA | 349 |
| Pro | Thr | Lys | Pro | Ile | Glu | Gly | Gln | Lys | Thr | Gly | Thr | Ser | Gly | Leu | Arg | |
| | | | | 80 | | | | | 85 | | | | | 90 | | |
| AAA | AAG | GTG | AAA | GTG | TTT | AAG | CAA | GAA | AAT | TAC | CTT | GCA | AAT | TGG | ATT | 397 |
| Lys | Lys | Val | Lys | Val | Phe | Lys | Gln | Glu | Asn | Tyr | Leu | Ala | Asn | Trp | Ile | |
| | | | 95 | | | | | 100 | | | | | 105 | | | |
| CAG | GCA | CTG | TTT | AAT | TCG | TTG | CCG | CCG | GAG | GAT | TAC | AAG | AAT | GGA | TTG | 445 |
| Gln | Ala | Leu | Phe | Asn | Ser | Leu | Pro | Pro | Glu | Asp | Tyr | Lys | Asn | Gly | Leu | |
| | | 110 | | | | | 115 | | | | | 120 | | | | |
| TTG | GTT | TTG | GGA | GGC | GAT | GGT | CGA | TAC | TTC | AAT | AAA | GAA | GCT | GCA | CAG | 493 |
| Leu | Val | leu | Gly | Gly | Asp | Gly | Arg | Tyr | Phe | Asn | Lys | Glu | Ala | Ala | Gln | |
| | 125 | | | | 130 | | | | | 135 | | | | | | |
| ATA | ATA | ATC | AAG | ATT | GCT | GCT | GGA | AAT | GGT | GTT | GGA | AAA | ATT | CTG | GTT | 541 |
| Ile | Ile | Ile | Lys | Ile | Ala | Ala | Gly | Asn | Gly | Val | Gly | Lys | Ile | Leu | Val | |
| 140 | | | | 145 | | | | | 150 | | | | | 155 | | |
| GGG | AAG | GAA | GGG | ATA | TTG | TCA | ACG | CCA | GCC | GTT | TCT | GCT | GTG | ATA | AGG | 589 |
| Gly | Lys | Glu | Gly | Ile | Leu | Ser | Thr | Pro | Ala | Val | Ser | Ala | Val | Ile | Arg | |
| | | | | 160 | | | | | 165 | | | | | 170 | | |

Fig. 1B

| | |
|---|---|
| AAG AGA GAG GCA AAT GGT GGG TTT ATC ATG AGT GCG AGC CAT AAC CCT<br>Lys Arg Glu Ala Asn Gly Gly Phe Ile Met Ser Ala Ser His Asn Pro<br>               175                       180                    185 | 637 |
| GGT GGA CCT GAA TAT GAT TGG GGT ATT AAG TTT AAT TAC AGT AGC GGA<br>Gly Gly Pro Glu Tyr Asp Trp Gly Ile Lys Phe Asn Tyr Ser Ser Gly<br>               190                       195                    200 | 685 |
| CAA CCT GCA CCA GAA TCC ATC ACC GAC AAG ATT TAC GGA AAC ACC CTA<br>Gln Pro Ala Pro Glu Ser Ile Thr Asp Lys Ile Tyr Gly Asn Thr Leu<br>               205                       210                    215 | 733 |
| TCG ATT TCT GAG ATA AAG ATT GCT GAT ATT CCC GAT GTT GAC TTA TCA<br>Ser Ile Ser Glu Ile Lys Ile Ala Asp Ile Pro Asp Val Asp Leu Ser<br>220                    225                       230                    235 | 781 |
| AAT GTT GGA GTT ACG AAA TTC GGA AGC TTC AGT GTG GAA GTA ATA GAC<br>Asn Val Gly Val Thr Lys Phe Gly Ser Phe Ser Val Glu Val Ile Asp<br>               240                       245                    250 | 829 |
| CCA GTT TCT GAT TAC CTG GAG TTA TTG GAG ACA GTG TTC GAT TTT CAG<br>Pro Val Ser Asp Tyr Leu Glu Leu Leu Glu Thr Val Phe Asp Phe Gln<br>               255                       260                    265 | 877 |
| CTA ATC AAA AGT CTT ATT TCA CGG CCA GAT TTT AGG TTT ACA TTT GAT<br>Leu Ile Lys Ser Leu Ile Ser Arg Pro Asp Phe Arg Phe Thr Phe Asp<br>               270                       275                    280 | 925 |
| GCC ATG CAT GCA GTT GCC GGT GCT TAT GCA ACA CCC ATT TTC GTT GAT<br>Ala Met His Ala Val Ala Gly Ala Tyr Ala Thr Pro Ile Phe Val Asp<br>               285                       290                    295 | 973 |
| AAA CTT GGT GCT AGT CCG GAT TCA ATT TCA AAT GGA ATA CCT TTG GAA<br>Lys Leu Gly Ala Ser Pro Asp Ser Ile Ser Asn Gly Ile Pro Leu Glu<br>300                    305                       310                    315 | 1021 |
| GAT TTT GGA CAT GGT CAT CCT GAT CCT AAT CTA ACA TAC GCA AAG GAT<br>Asp Phe Gly His Gly His Pro Asp Pro Asn Leu Thr Tyr Ala Lys Asp<br>                    320                       325                    330 | 1069 |
| CTT GTC AAT ATT ATG TAT GCT GAA AAC GGA CCT GAT TTT GGT GCC GCT<br>Leu Val Asn Ile Met Tyr Ala Glu Asn Gly Pro Asp Phe Gly Ala Ala<br>               335                       340                    345 | 1117 |
| AGT GAT GGT GAT GGT GAT AGA AAT ATG ATT TTG GGA ACA AGT TTC TTC<br>Ser Asp Gly Asp Gly Asp Arg Asn Met Ile Leu Gly Thr Ser Phe Phe<br>               350                       355                    360 | 1165 |

Fig. 1C

```
GTA ACT CCT TCA GAC TCT GTA GCC GTT ATT GCA GCC AAT GCA AAA GAA      1213
Val Thr Pro Ser Asp Ser Val Ala Val Ile Ala Ala Asn Ala Lys Glu
    365             370             375

GCG ATT AAG TAC TTT AAG GAC AGT ATC AAG GGT CTT GCA CGA TCA ATG      1261
Ala Ile Pro Tyr Phe Lys Asp Ser Ile Lys Gly Leu Ala Arg Ser Met
380             385             390             395

CCG ACA AGC GGT GCT CTA GAT AGA GTT GCT GAA AAG TTG AAC CTC CCT      1309
Pro Thr Ser Gly Ala Leu Asp Arg Val Ala Glu Lys Leu Asn Leu Pro
                400             405             410

TTT TTT GAG GTT CCC ACT GGT TGG AAA TTC TTT GGT AAT CTT ATG GAT      1357
Phe Phe Glu Val Pro Thr Gly Trp Lys Phe Phe Gly Asn Leu Met Asp
            415             420             425

GCT GGA AAT CTG TCG ATT TGC GGG GAA GAG AGT TTT GGA ACA GGT TCT      1405
Ala Gly Asn Leu Ser Ile Cys Gly Glu Glu Ser Phe Gly Thr Gly Ser
        430             435             440

GAC CAC ATT CGT GAG AAA GAC GGA ATC TGG GCT GTA TTA GCT TGG CTT      1453
Asp His Ile Arg Glu Lys Asp Gly Ile Trp Ala Val Leu Ala Trp Leu
    445             450             455

TCG ATT ATT GCT CAC CGC AAC AAA GAC ACG AAA CCA GGG GAG AAA TTG      1501
Ser Ile Ile Ala His Arg Asn Lys Asp Thr Lys Pro Gly Glu Lys Leu
460             465             470             475

GTC TCT GTG TCT GAT GTT GTG AAG GAG CAT TGG GCA ACC TAT GGT AGA      1549
Val Ser Val Ser Asp Val Val Lys Glu His Trp Ala Thr Tyr Gly Arg
                480             485             490

AAT TTC TTT TCT AGA TAC GAT TAC GAG GAA TGT GAA TCC GAA GGC GCA      1597
Asn Phe Phe Ser Arg Tyr Asp Tyr Glu Glu Cys Glu Ser Glu Gly Ala
            495             500             505

AAT AAG ATG ATA GAG TAC CTA CGA GAG CTT TTG TCG AAG AGC AAG CCT      1645
Asn Lys Met Ile Glu Tyr Leu Arg Glu Leu Leu Ser Lys Ser Lys Pro
        510             515             520

GGT GAT AAG TAT GGA AGT TAC GTC CTC CAG TTT GCC GAT GAT TAT ACA      1693
Gly Asp Lys Tyr Gly Ser Tyr Val Leu Gln Phe Ala Asp Asp Tyr Thr
    525             530             535

TAC ACT GAT CCT GTA GAT GGA AGT GTA GTA TCA AAA CAA GGG GTT CGG      1741
Tyr Thr Asp Pro Val Asp Gly Ser Val Val Ser Lys Gln Gly Val Arg
540             545             550             555
```

Fig. 1D

```
TTT GTT TTC ACC GAT GGT TCA AGA ATT ATT TAC CGT TTA TCA GGA ACG      1789
Phe Val Phe Thr Asp Gyl Ser Arg Ile Ile Tyr Arg Leu Ser Gly Thr
            560             565             570

GGT TCT GCT GGT GCA ACT GTT AGA GTG TAT ATC GAA CAG TTT GAA CCA      1837
Gly Ser Ala Gly Ala Thr Val Arg Val Tyr Ile Glu Gln Phe Glu Pro
            575             580             585

GAT GTT TCT AAA CAA GAC GTC GAT GCT CAA ATT GCC TTG AAA CCA TTA      1885
Asp Val Ser Lys His Asp Val Asp Ala Gln Ile Ala Leu Lys Pro Leu
            590             595             600

ATA GAT TTA GCA TTA TCT GTT TCA AAG CTC AAA GAC TTC ACA GGG AGA      1933
Ile Asp Leu Ala Leu Ser Val Ser Lys Leu Lys Asp Phe Thr Gly Arg
            605             610             615

GAG AAG CCT ACA GTC ATC ACT TAA TATAAGTTTG GTTTTTCATT TTCAGTTTTG     1987
Glu Lys Pro Thr Val Ile Thr *
620             625

GTTATTTTTC CACTTTGGAG CTTAGCATCT TTTTTGTATA ATATGATATT TTGTATTTAC    2047

TTTCAAGAAA ATGAAGTATC ATTGTGTAAC AGAATAAATA ATGGTATTAA TAATAGCTAG    2107

CTTCTATGCA GAGAAGTTGT TCTTTTCAAA AAAAAAAAAA AAAAAAAAAA AAAAAAAAAA    2167

AAAAAAAAAA AAAAA                                                     2182
```

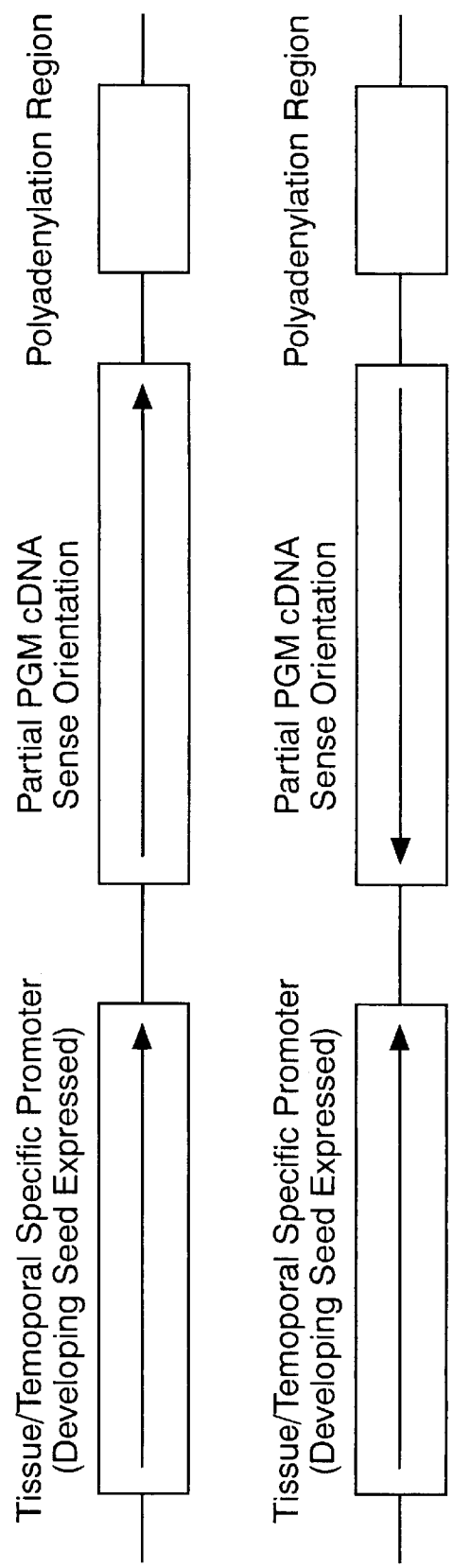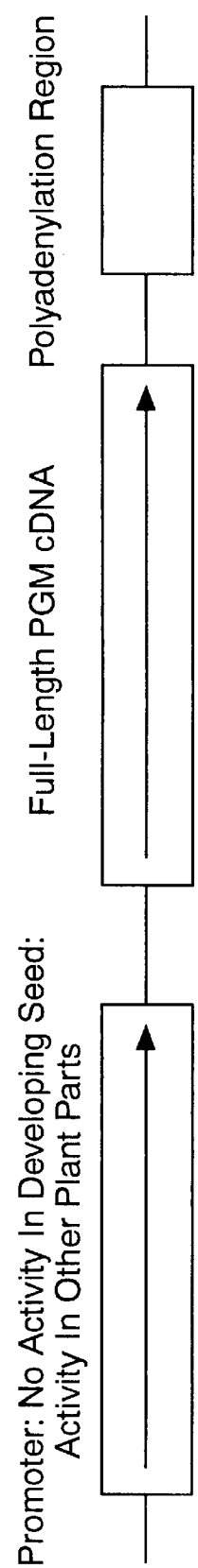

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO: 1:

ACNGCNWSNC AYAAYCC                           17

(2) INFORMATION FOR SEQ ID NO: 2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO: 2:

CKRTCNCCRT CNCCRTCRAA NGC                   23

(2) INFORMATION FOR SEQ ID NO: 3:

(i) SEQUENCE CHARACTERISTICS:
      (A) LENGTH: 2182 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION:77..1957

(xi) SEQUENCE DESCRIPTION: SEQ ID NO: 3:

```
CAAACACATA GTTAAACAAA AAACACTCTC TCTTGACTCT TCGAAGAAAA AGTTGTCACT        60

GTTACAGACT CGATCA ATG GCT TTC TGT TAC AGA CTC GAC AAC TTC ATC          109
              Met Ala Phe Cys Tyr Arg Leu Asp Asn Phe Ile
                1               5                  10
```

```
ATC TCT GCG TTT AAA CCC AAA CAC TCA AAT GTC CCA CTT TCA ATT CAT      157
Ile Ser Ala Phe Lys Pro Lys His Ser Asn Val Pro Leu Ser Ile His
            15              20                  25

CAT TCA TCA TCC AAT TTT CCT TCT TTC AAA GTT CAA AAC TTT CCT TTC      205
His Ser Ser Ser Asn Phe Pro Ser Phe Lys Val Gln Asn Phe Pro Phe
        30              35                  40

AGG GTT CGC TAT AAT TCA GCT ATT AGA GCC ACT TCA TCT TCC TCT TCT      253
Arg Val Arg Tyr Asn Ser Ala Ile Arg Ala Thr Ser Ser Ser Ser Ser
    45              50                  55

ACT CCC ACA ACC ATT GCA GAA CCT AAT GAC ATT AAG ATT AAC TCT ATT      301
Thr Pro Thr Thr Ile Ala Glu Pro Asn Asp Ile Lys Ile Asn Ser Ile
60              65                  70                  75

CCT ACT AAA CCT ATT GAA GGA CAA AAA ACT GGT ACC AGT GGT CTA AGA      349
Pro Thr Lys Pro Ile Glu Gly Gln Lys Thr Gly Thr Ser Gly Leu Arg
            80                  85                  90

AAA AAG GTG AAA GTG TTT AAG CAA GAA AAT TAC CTT GCA AAT TGG ATT      397
Lys Lys Val Lys Val Phe Lys Gln Glu Asn Tyr Leu Ala Asn Trp Ile
                95                  100                 105

CAG GCA CTG TTT AAT TCG TTG CCG CCG GAG GAT TAC AAG AAT GGA TTG      445
Gln Ala Leu Phe Asn Ser Leu Pro Pro Glu Asp Tyr Lys Asn Gly Leu
            110                 115                 120

TTG GTT TTG GGA GGC GAT GGT CGA TAC TTC AAT AAA GAA GCT GCA CAG      493
Leu Val Leu Gly Gly Asp Gly Arg Tyr Phe Asn Lys Glu Ala Ala Gln
        125                 130                 135

ATA ATA ATC AAG ATT GCT GCT GGA AAT GGT GTT GGA AAA ATT CTG GTT      541
Ile Ile Ile Lys Ile Ala Ala Gly Asn Gly Val Gly Lys Ile Leu Val
140                 145                 150                 155

GGG AAG GAA GGG ATA TTG TCA ACG CCA GCC GTT TCT GCT GTG ATA AGG      589
Gly Lys Glu Gly Ile Leu Ser Thr Pro Ala Val Ser Ala Val Ile Arg
                160                 165                 170

AAG AGA GAG GCA AAT GGT GGG TTT ATC ATG AGT GCG AGC CAT AAC CCT      637
Lys Arg Glu Ala Asn Gly Gly Phe Ile Met Ser Ala Ser His Asn Pro
            175                 180                 185

GGT GGA CCT GAA TAT GAT TGG GGT ATT AAG TTT AAT TAC AGT AGC GGA      685
Gly Gly Pro Glu Tyr Asp Trp Gly Ile Lys Phe Asn Tyr Ser Ser Gly
        190                 195                 200

CAA CCT GCA CCA GAA TCC ATC ACC GAC AAG ATT TAC GGA AAC ACC CTA      733
Gln Pro Ala Pro Glu Ser Ile Thr Asp Lys Ile Tyr Gly Asn Thr Leu
    205                 210                 215

TCG ATT TCT GAG ATA AAG ATT GCT GAT ATT CCC GAT GTT GAC TTA TCA      781
Ser Ile Ser Glu Ile Lys Ile Ala Asp Ile Pro Asp Val Asp Leu Ser
220                 225                 230                 235

AAT GTT GGA GTT ACG AAA TTC GGA AGC TTC AGT GTG GAA GTA ATA GAC      829
Asn Val Gly Val Thr Lys Phe Gly Ser Phe Ser Val Glu Val Ile Asp
                240                 245                 250

CCA GTT TCT GAT TAC CTG GAG TTA TTG GAG ACA GTG TTC GAT TTT CAG      877
Pro Val Ser Asp Tyr Leu Glu Leu Leu Glu Thr Val Phe Asp Phe Gln
            255                 260                 265

CTA ATC AAA AGT CTT ATT TCA CGG CCA GAT TTT AGG TTT ACA TTT GAT      925
Leu Ile Lys Ser Leu Ile Ser Arg Pro Asp Phe Arg Phe Thr Phe Asp
        270                 275                 280

GCC ATG CAT GCA GTT GCC GGT GCT TAT GCA ACA CCC ATT TTC GTT GAT      973
Ala Met His Ala Val Ala Gly Ala Tyr Ala Thr Pro Ile Phe Val Asp
    285                 290                 295

AAA CTT GGT GCT AGT CCG GAT TCA ATT TCA AAT GGA ATA CCT TTG GAA     1021
Lys Leu Gly Ala Ser Pro Asp Ser Ile Ser Asn Gly Ile Pro Leu Glu
300                 305                 310                 315

GAT TTT GGA CAT GGT CAT CCT GAT CCT AAT CTA ACA TAC GCA AAG GAT     1069
Asp Phe Gly His Gly His Pro Asp Pro Asn Leu Thr Tyr Ala Lys Asp
                320                 325                 330
```

```
CTT GTC AAT ATT ATG TAT GCT GAA AAC GGA CCT GAT TTT GGT GCC GCT     1117
Leu Val Asn Ile Met Tyr Ala Glu Asn Gly Pro Asp Phe Gly Ala Ala
            335                 340                 345

AGT GAT GGT GAT GGT GAT AGA AAT ATG ATT TTG GGA ACA AGT TTC TTC     1165
Ser Asp Gly Asp Gly Asp Arg Asn Met Ile Leu Gly Thr Ser Phe Phe
        350                 355                 360

GTA ACT CCT TCA GAC TCT GTA GCC GTT ATT GCA GCC AAT GCA AAA GAA     1213
Val Thr Pro Ser Asp Ser Val Ala Val Ile Ala Ala Asn Ala Lys Glu
    365                 370                 375

GCG ATT CCG TAC TTT AAG GAC AGT ATC AAG GGT CTT GCA CGA TCA ATG     1261
Ala Ile Pro Tyr Phe Lys Asp Ser Ile Lys Gly Leu Ala Arg Ser Met
380                 385                 390                 395

CCG ACA AGC GGT GCT CTA GAT AGA GTT GCT GAA AAG TTG AAC CTC CCT     1309
Pro Thr Ser Gly Ala Leu Asp Arg Val Ala Glu Lys Leu Asn Leu Pro
            400                 405                 410

TTT TTT GAG GTT CCC ACT GGT TGG AAA TTC TTT GGT AAT CTT ATG GAT     1357
Phe Phe Glu Val Pro Thr Gly Trp Lys Phe Phe Gly Asn Leu Met Asp
        415                 420                 425

GCT GGA AAT CTG TCG ATT TGC GGG GAA GAG AGT TTT GGA ACA GGT TCT     1405
Ala Gly Asn Leu Ser Ile Cys Gly Glu Glu Ser Phe Gly Thr Gly Ser
    430                 435                 440

GAC CAC ATT CGT GAG AAA GAC GGA ATC TGG GCT GTA TTA GCT TGG CTT     1453
Asp His Ile Arg Glu Lys Asp Gly Ile Trp Ala Val Leu Ala Trp Leu
    445                 450                 455

TCG ATT ATT GCT CAC CGC AAC AAA GAC ACG AAA CCA GGG GAG AAA TTG     1501
Ser Ile Ile Ala His Arg Asn Lys Asp Thr Lys Pro Gly Glu Lys Leu
460                 465                 470                 475

GTC TCT GTG TCT GAT GTT GTG AAG GAG CAT TGG GCA ACC TAT GGT AGA     1549
Val Ser Val Ser Asp Val Val Lys Glu His Trp Ala Thr Tyr Gly Arg
            480                 485                 490

AAT TTC TTT TCT AGA TAC GAT TAC GAG GAA TGT GAA TCC GAA GGC GCA     1597
Asn Phe Phe Ser Arg Tyr Asp Tyr Glu Glu Cys Glu Ser Glu Gly Ala
        495                 500                 505

AAT AAG ATG ATA GAG TAC CTA CGA GAG CTT TTG TCG AAG AGC AAG CCT     1645
Asn Lys Met Ile Glu Tyr Leu Arg Glu Leu Leu Ser Lys Ser Lys Pro
    510                 515                 520

GGT GAT AAG TAT GGA AGT TAC GTC CTC CAG TTT GCC GAT GAT TAT ACA     1693
Gly Asp Lys Tyr Gly Ser Tyr Val Leu Gln Phe Ala Asp Asp Tyr Thr
525                 530                 535

TAC ACT GAT CCT GTA GAT GGA AGT GTA GTA TCA AAA CAA GGG GTT CGG     1741
Tyr Thr Asp Pro Val Asp Gly Ser Val Val Ser Lys Gln Gly Val Arg
540                 545                 550                 555

TTT GTT TTC ACC GAT GGT TCA AGA ATT ATT TAC CGT TTA TCA GGA ACG     1789
Phe Val Phe Thr Asp Gly Ser Arg Ile Ile Tyr Arg Leu Ser Gly Thr
            560                 565                 570

GGT TCT GCT GGT GCA ACT GTT AGA GTG TAT ATC GAA CAG TTT GAA CCA     1837
Gly Ser Ala Gly Ala Thr Val Arg Val Tyr Ile Glu Gln Phe Glu Pro
        575                 580                 585

GAT GTT TCT AAA CAC GAC GTC GAT GCT CAA ATT GCC TTG AAA CCA TTA     1885
Asp Val Ser Lys His Asp Val Asp Ala Gln Ile Ala Leu Lys Pro Leu
    590                 595                 600

ATA GAT TTA GCA TTA TCT GTT TCA AAG CTC AAA GAC TTC ACA GGG AGA     1933
Ile Asp Leu Ala Leu Ser Val Ser Lys Leu Lys Asp Phe Thr Gly Arg
605                 610                 615

GAG AAG CCT ACA GTC ATC ACT TAA TATAAGTTTG GTTTTTCATT TTCAGTTTTG    1987
Glu Lys Pro Thr Val Ile Thr *
620                 625

GTTATTTTTC CACTTTGGAG CTTAGCATCT TTTTTGTATA ATATGATATT TTGTATTTAC   2047
```

```
TTTCAAGAAA ATGAAGTATC ATTGTGTAAC AGAATAAATA ATGGTATTAA TAATAGCTAG      2107

CTTCTATGCA GAGAAGTTGT TCTTTTCAAA AAAAAAAAAA AAAAAAAAAA AAAAAAAAAA      2167

AAAAAAAAAA AAAAA                                                       2182
```

(2) INFORMATION FOR SEQ ID NO: 4:

(i) SEQUENCE CHARACTERISTICS:
        (A) LENGTH: 626 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ala Phe Cys Tyr Arg Leu Asp Asn Phe Ile Ile Ser Ala Phe Lys
  1               5                  10                  15

Pro Lys His Ser Asn Val Pro Leu Ser Ile His His Ser Ser Ser Asn
             20                  25                  30

Phe Pro Ser Phe Lys Val Gln Asn Phe Pro Phe Arg Val Arg Tyr Asn
         35                  40                  45

Ser Ala Ile Arg Ala Thr Ser Ser Ser Ser Thr Pro Thr Thr Ile
     50                  55                  60

Ala Glu Pro Asn Asp Ile Lys Ile Asn Ser Ile Pro Thr Lys Pro Ile
 65                  70                  75                  80

Glu Gly Gln Lys Thr Gly Thr Ser Gly Leu Arg Lys Val Lys Val
                 85                  90                  95

Phe Lys Gln Glu Asn Tyr Leu Ala Asn Trp Ile Gln Ala Leu Phe Asn
                100                 105                 110

Ser Leu Pro Pro Glu Asp Tyr Lys Asn Gly Leu Leu Val Leu Gly Gly
            115                 120                 125

Asp Gly Arg Tyr Phe Asn Lys Glu Ala Ala Gln Ile Ile Ile Lys Ile
        130                 135                 140

Ala Ala Gly Asn Gly Val Gly Lys Ile Leu Val Gly Lys Glu Gly Ile
145                 150                 155                 160

Leu Ser Thr Pro Ala Val Ser Ala Val Ile Arg Lys Arg Glu Ala Asn
                165                 170                 175

Gly Gly Phe Ile Met Ser Ala Ser His Asn Pro Gly Gly Pro Glu Tyr
            180                 185                 190

Asp Trp Gly Ile Lys Phe Asn Tyr Ser Ser Gly Gln Pro Ala Pro Glu
        195                 200                 205

Ser Ile Thr Asp Lys Ile Tyr Gly Asn Thr Leu Ser Ile Ser Glu Ile
    210                 215                 220

Lys Ile Ala Asp Ile Pro Asp Val Asp Leu Ser Asn Val Gly Val Thr
225                 230                 235                 240

Lys Phe Gly Ser Phe Ser Val Glu Val Ile Asp Pro Val Ser Asp Tyr
                245                 250                 255

Leu Glu Leu Leu Glu Thr Val Phe Asp Phe Gln Leu Ile Lys Ser Leu
            260                 265                 270

Ile Ser Arg Pro Asp Phe Arg Phe Thr Phe Asp Ala Met His Ala Val
        275                 280                 285

Ala Gly Ala Tyr Ala Thr Pro Ile Phe Val Asp Lys Leu Gly Ala Ser
    290                 295                 300

Pro Asp Ser Ile Ser Asn Gly Ile Pro Leu Glu Asp Phe Gly His Gly
305                 310                 315                 320

His Pro Asp Pro Asn Leu Thr Tyr Ala Lys Asp Leu Val Asn Ile Met
```

```
                        325                 330                 335
Tyr Ala Glu Asn Gly Pro Asp Phe Gly Ala Ala Ser Asp Gly Asp Gly
                340                 345                 350
Asp Arg Asn Met Ile Leu Gly Thr Ser Phe Phe Val Thr Pro Ser Asp
            355                 360                 365
Ser Val Ala Val Ile Ala Ala Asn Ala Lys Glu Ala Ile Pro Tyr Phe
        370                 375                 380
Lys Asp Ser Ile Lys Gly Leu Ala Arg Ser Met Pro Thr Ser Gly Ala
385                 390                 395                 400
Leu Asp Arg Val Ala Glu Lys Leu Asn Leu Pro Phe Phe Glu Val Pro
                405                 410                 415
Thr Gly Trp Lys Phe Phe Gly Asn Leu Met Asp Ala Gly Asn Leu Ser
                420                 425                 430
Ile Cys Gly Glu Glu Ser Phe Gly Thr Gly Ser Asp His Ile Arg Glu
            435                 440                 445
Lys Asp Gly Ile Trp Ala Val Leu Ala Trp Leu Ser Ile Ile Ala His
        450                 455                 460
Arg Asn Lys Asp Thr Lys Pro Gly Glu Lys Leu Val Ser Val Ser Asp
465                 470                 475                 480
Val Val Lys Glu His Trp Ala Thr Tyr Gly Arg Asn Phe Phe Ser Arg
                485                 490                 495
Tyr Asp Tyr Glu Glu Cys Glu Ser Glu Gly Ala Asn Lys Met Ile Glu
                500                 505                 510
Tyr Leu Arg Glu Leu Leu Ser Lys Ser Lys Pro Gly Asp Lys Tyr Gly
            515                 520                 525
Ser Tyr Val Leu Gln Phe Ala Asp Asp Tyr Thr Tyr Thr Asp Pro Val
        530                 535                 540
Asp Gly Ser Val Val Ser Lys Gln Gly Val Arg Phe Val Phe Thr Asp
545                 550                 555                 560
Gly Ser Arg Ile Ile Tyr Arg Leu Ser Gly Thr Gly Ser Ala Gly Ala
                565                 570                 575
Thr Val Arg Val Tyr Ile Glu Gln Phe Glu Pro Asp Val Ser Lys His
                580                 585                 590
Asp Val Asp Ala Gln Ile Ala Leu Lys Pro Leu Ile Asp Leu Ala Leu
            595                 600                 605
Ser Val Ser Lys Leu Lys Asp Phe Thr Gly Arg Glu Lys Pro Thr Val
        610                 615                 620
Ile Thr
625
```

METHOD FOR INCREASING SUCROSE CONTENT OF PLANTS

This application is the national phase of international application PCT/EP97/03613 filed Jul. 3, 1997 which designated the U.S. and claims priority to Great Britain application 9702653.8, filed Feb. 10, 1997 and Great Britain application 9615103.0, filed Jul. 18, 1996 and U.S. provisional application No. 60/021,410, filed Jul. 9, 1996.

FIELD OF THE INVENTION

This invention relates to plants, and particularly concerns peas (*Pisum sativum* L.), products derived therefrom and methods for genetically altering them, particularly for affecting the sucrose and starch content.

BACKGROUND TO THE INVENTION

Peas are an important crop plant, producing products used for human and animal consumption. The seeds of the pea plant can be harvested either in a dry mature form or in an immature state, with the precise stage of maturity varying according to the end use. Within each of these two categories there are a number of specialized uses and markets. The dry mature seed is used extensively as animal feed, directly as human food and as an ingredient of a variety of prepared foods. Those harvested in an immature form are used directly as a fresh vegetable or are processed by being canned, dehydrated or frozen. Peas harvested by machine at an immature stage for quick freezing are referred to in the art as vining peas.

Conventional cross-breeding methods have been used to develop new varieties and cultivars in order to satisfy different local or national requirements or niche markets. They include varieties with different colour, texture, sugar and starch contents, and size of seed.

The pea is also a useful experimental organism, and the pea is well characterised with many known variants.

Characterised mutants cover the whole spectrum of plant development, morphology and physiology. Some mutants may have had characters which were desirable to man to improve the pea crop and as such have been selected for.

The 'Rugosus' Loci

The r and rb Loci

Mendel, in his classic studies of genetics showed that the wrinkled-seeded phenotype of the r (rugosus) mutant is a recessive trait which fitted his newly formulated laws of inheritance. The r mutant became a popular tool for geneticists both classical and modern and is now well characterised. The terms rr, Rr and RR have been used to describe the homozygous recessive, heterozygous and homozygous dominant genotypes, respectively, with the rr genotype leading to the mature seeds being wrinkled in appearance (hence rugosus, which is the Latin word for wrinkled) The presence of the dominant allele (R) causes the mature seeds to be smooth. The original mutation is believed to have arisen spontaneously at the beginning of the seventeenth century. The seeds of the r mutant contain a lower proportion of starch than the wild-type (about 30% dry weight as opposed to about 50%), with the starch composition being altered to contain a higher proportion of amylose and smaller proportion of amylopectin (with about 70% of dry weight of the starch of mutant seeds being amylose as opposed to 38% of the wild-type starch). The effect of the mutation in the r gene has been shown to be caused by reduced activity of one of the branching enzyme isoforms (SBE1). The gene has been cloned and sequenced, and a 0.8 kb transposon-like insertion has been found to be present in the mutant gene.

A second recessive rugosus locus termed rb has also been characterised. Mutants homozygous recessive at this locus have a wrinkled-seeded phenotype similar to that of rr plants, although the amount of starch and its composition differs in that starch comprises about 36% of the dry eight of the seed, about 23% of which is amylose. The rb mutation has been found to result in reduced activity in the enzyme ADP glucose pyrophosphorylase. Purification of the enzyme and western-blotting experiments have revealed the absence of one of the four polypeptide subunits present in the wild-type enzyme. Manipulation by reduction or suppression of the activity of ADP-glucose pyrophosphorylase (ADPG-PPase) to give an increased level of sucrose in the plant has been described in U.S. Pat. No. 5,498,831 (Burgess et al).

New Rugosus Loci

A mutagenesis programme was carried out by Wang et al, as described in Plant Breeding 105, 311–320 (1990) "An Analysis of Seed Development in *Pisum sativum*. XIII The Chemical Induction of Storage Product Mutants". The programme employed chemical mutagenesis using ethyl methanesulphonate (EMS) or N-methyl-N-nitrosourea (MNU). Peas have been shown to be susceptible to mutation by chemical agents and these particular mutagens are likely to cause point mutations by alkylation. Twenty thousand phenotypically round genetically wild type (RR) seeds were treated with either of the above chemicals, these being termed M1 (mutagenised) seed. M1 seed gave rise to M1 plants bearing M2 seed. M2 seed gave rise to M2 plants bearing M3 seed. M3 seeds were analysed for storage product content.

Seeds which appeared wrinkled selected from the M3 generation had a wide range of starch content, from 0–60% as a proportion of the dry weight of the mature seed. Within the starch of these seeds, the amylose content ranged from 0–80%. The lipid and protein contents of the M3 seeds also appeared to be more varied than had been previously observed in peas, with a lipid content from 1–8% of the dry weight and a protein range of 24–48%, the latter showing a higher maxima than the existing variation of between 24 and 41%. The conclusion from the initial analyses of the M3 seeds was that new rugosus mutants had been induced and that it was likely that some would be mutants affecting starch biosynthesis.

The new mutant lines were each designated by a 'SIM' number (SIM=Seed: Induced Mutant). Preliminary allelism tests to the r and rb loci revealed that some of the SIM lines were not allelic to either of these loci and therefore were probably mutants affecting other enzymes in the starch pathway. Other lines were found to be allelic to r or rb and therefore these lines represent new mutant alleles of these loci (see Wang and Hedley, Seed Science Research (1991) 1, 3–14, "Seed Development in peas: knowing your three "r's" (or four of five)"). More detailed complementation analyses involving a complete diallel cross between 24 of the SIM lines and lines with rr and rbrb genotypes placed the mutants into five groups, two of which contained the original rugosus mutants (see Hedley and Wang, Aspects of Applied Biology 27 (1991) Production and protection of legumes, 205–209, "Adding value to the pea crop by genetically manipulating the storage product composition of the seed"). Recently, grouping of the SIM lines has been completed and the three new rugosus loci have been assigned the gene symbols rug3, rug4 and rug5 in accordance with the Pisum Genetics Association (see Wang and Hedley, 1993, Pisum Genetics 25, 64–70, "Seed Mutants in Pisum"). The five complementation groups are shown in Table 1.

TABLE 1

| Group Gene Symbol | 1 r | 2 rb | 3 rug3 | 4 rug4 | 5 rug5 |
|---|---|---|---|---|---|
| SIM Lines | 53 | 14 | 1 | 11 | 51 |
|  | 54 | 15 | 32 | 91 | 52 |
|  | 55 | 16 | 41 | 201 | 81 |
|  | 56 | 101 | 42 |  |  |
|  | 57 | 102 | 43 |  |  |
|  | 58 | 103 |  |  |  |
|  | 59 | 103W |  |  |  |
|  | 61 |  |  |  |  |
|  | 71 |  |  |  |  | rug3

Preliminary analysis of the storage product content of the SIM lines showed that those belonging to the rug3 group had a dramatically reduced starch content in the mature seed by comparison to wild-type, round-seeded lines. The mutants in this group appeared to have between 1 and 20% starch as a proportion of the dry weight of the mature seed, compared with about 55% in round seeds (see Wang and Hedley, 1991 referred to above). In addition, these lines seemed to show a complete absence of amylose from the starch that was present. Such a phenotype had never been observed previously in pea.

The SIM lines belonging to the rug3 complementation group have been assingned gene symbols as shown in Table 2 (Wang and Hedley, 1993 referred to above).

TABLE 2

| SIM number | Gene Symbol |
|---|---|
| 1 | rug3$^a$ |
| 32 | rug3$^b$ |
| 41 | rug3$^c$ |
| 42 | rug3$^d$ |
| 43 | rug3$^a$ |

Peas of the rug3rug3 genotype (which are referred to herein as rug3 peas for simplicity) are of scientific and potential commercial interest because of the low levels of starches of unusual nature, and also because of their high protein and lipid contents. See, for example, Hedley and Wang, Aspects of Applied Biology 27 (1991) 205–209, Hedley and Wang, Agro-Food Industry Hi-Tech (January/February 1993) 14–17, Farmers Weekly, Apr. 19, 1991, 54–57.

The present invention is based on the unexpected discovery that rug3 peas produce seeds that at the end of the vining period have higher sucrose levels than those of conventional vining pea varieties thus are particularly suitable for human consumption.

Pea seeds intended for vining should combine sweetness and acceptable texture. It has been found that rug3 peas produce seeds that maintain the combination of acceptably high levels of sucrose with suitably low levels of starch over a considerably longer period of time than known pea varieties. Thus, rug3 peas seeds may suitably be vined at a stage of maturity which for conventional pea varieties would be considered too advanced for freezing and suitable only for canning. This is of commercial interest as the period of suitability for vining, generally referred to as the harvest window, is therefore extended.

The rug3 mutation has been found by the present inventors to be associated with a substantial reduction in the activity of the enzyme plastidial phosphoglucomutase (PGM (p)). PGM(p) activity has been found to be reduced to 10% or less of the activity levels in conventional pea lines, and in the extreme case PGM(p) activity is substantially completely lacking.

The significance of a lack of PGM(p) activity is that in the plastid, the interconversion of glucose-1-phosphate and glucose-6-phosphate cannot occur. The importance of this reaction in the synthesis of starch is that glucose-1-phosphate is the substrate for the committed pathway of starch synthesis. It is thought that in pea, glucose-1-phosphate cannot be transported into the plastids (Hill and Smith, Planta 185, 91, 1991; Borchert et al, Plant Physiology 101, 303–312, 1993) and that the production of glucose-1-phosphate in the plastids is dependent on PGM(p) activity. Without a supply of glucose-1-phosphate, the synthesis of starch cannot take place. Sugar and starch metabolism are known to be related in plants and by altering the levels of an enzyme involved in the starch synthesis pathway, it may be possible to alter the level of sugar in the plant.

The cDNA sequence encoding the pea phophoglucomutase (PGM) enzyme has been cloned from immature pea embryos and has been found to exhibit considerable regions of homology throughout the gene with known cDNA PGM sequences cloned from other species. Further, genetic segregation analysis has shown that the rug3 mutation maps very closely to, or on top of, the PGM(p) gene, providing evidence that the mutation affects the PGM(p) gene. By suppressing or reducing PGM expression in pea plants or other plants, the sucrose content of the plant may be increased.

SUMMARY OF THE INVENTION

In one aspect, the present invention provides pea seeds having a sucrose content of greater than 6% by weight of the total weight of the seed as harvested at a tenderometer reading exceeding 120 tenderometer units.

Preferably, the sucrose content in the peas seeds according to the invention is greater than 7% by weight of the total weight of the seed.

Peas with the rug3 phenotype can provide seeds having such a sucrose content which is significantly higher that the sucrose content of any conventional vining pea grown under equivalent conditions at the given state of maturity.

The stage of maturity appropriate for vining, can be estimated in a number of different ways, including the following:

1) By reference to the state of pod development. A skilled pea grower can determine relatively accurately by feeling a pea pod and seeds the state of maturity of the seeds and hence readiness for harvesting.
2) By reference to the number of days after flowering, having regard to weather conditions, particularly temperature. The stage of full flower is assessed by scoring the maturity of each flower on the first four flowering nodes. Once the full flower stage is reached, the harvest date can be approximately predicted in terms of average heat unit days from flowering to harvest having regard to the variety in question and its sowing date.
3) By reference to readings obtained with an instrument known as a tenderometer, which measures the tenderness of pea seeds in a way defined as an industry standard as determined by the independent body in the United Kingdom, Camden and Chorley Wood Food and Drink Research Association. For seeds for processing a tenderometer measurement in the range 95–120 tenderometer units is the accepted industry standard, with seeds for freezing preferably having a tenderometer measurement in the lower part of this range, as these are the most tender. With the current commercial varieties this is achieved by early harvesting, for which there is a yield penalty.

Due to the lack of starch the rug3 varieties may not give tenderometer readings that are exactly the same as those of conventional varieties, but indications from preliminary trials are that similar readings are obtained, implying that the tenderometer does not measure starch directly.

Sucrose and starch levels of seeds can be determined using known analytical techniques, including ion chromatography and spectrophotometric techniques.

In another aspect, the invention provides pea seeds wherein the ratio of sucrose content to starch content in the seed at vining is greater than 2.

Preferably, the ratio of sucrose to starch in pea seeds according to the invention at vining is greater than 5, more preferably greater than 10.

Mature dry seeds of rug3 peas also have a higher ratio of sucrose content to starch content compared to seeds of conventional pea lines. Conveniently this ratio is greater than 0.6, preferably greater than 1, especially greater than 2.

The ratio of sucrose content to starch content in the seed provides a useful indication of the deterioration in palatability of the seed for human consumption during maturation and hence its suitability for harvesting over an extended period. Conveniently, the ratio of sucrose content to starch content in pea seeds according to the invention remains above 0.6 during maturation from vining stage to mature dry form.

In order to maximise the yield of seed on vining, it is desirable to have as large a harvest window as possible. With conventional vining pea plants, seeds have a tenderometer reading within the critical range of 95–120 tenderometer units and sufficient sweetness appropriate for processing for only a very short time, in the order of ½ day in hot weather conditions to 2 days in cold weather. After this period the seeds are unacceptably tough and the sucrose content decreases to an extent where the seeds are not sweet enough. This very small harvest window presents serious practical difficulties in vining seeds on a commercial scale and, in practice, results in a substantial proportion of the crop being lost due to inability to vine in time. A discussion of production and harvesting of vining peas is given in Arthey D. 1985. Vining peas; processing and marketing. In Hebblethwaite P D, Heath M C, Dawkins T C K, eds. The pea crop. London: Butterworths, 433–440. The time of harvesting of the crop coincides with a point before the onset of rapid starch synthesis. Once harvested, a crop kept at ambient temperature must be processed rapidly, generally within three hours to prevent the occurrence of off flavours. Rug3 mutant peas are found to have a significantly larger harvest window, in the range of 1 day in hot conditions and 5 to 6 days in cold weather.

The invention thus provides a pea plant having an extended harvest window compared with conventional pea varieties.

There is further provided a method of extending the harvest window of a pea plant comprising growing a plant from a seed according to the invention.

The invention provides in a further aspect polynucleotides having the sequence of pea plastidial PGM (SEQ ID No. 3) shown in FIG. 1 or a functional equivalent thereof. Typically the polynucleotide is provided substantially free from other DNAs and RNAs with which the polynucleotide is naturally associated.

It will be appreciated that functionally equivalent nucleotide sequences are intended to include those sequences exhibiting at least 60% nucleotide homology, preferably at least 8%, more preferably at least 90% homology with the nucleotide sequence of FIG. 1. Such equivalent sequences are able to hybridise under standard laboratory conditions (e.g. Sambrook et al, Molecular Cloning: A Laboratory Manual, 2nd Edition, hereinafter "Sambrook") with the complement of the sequence shown in FIG. 1.

In addition, functionally equivalent sequences include those which are antisense equivalents of the sequence of nucleotides of FIG. 1. Such antisense equivalents are therefore able to hybridise with the sequence shown in FIG. 1 and are preferably able to interfere with expression of the sense sequence at the DNA and/or mRNA level.

Preferably the nucleotide sequence of the invention is comprised within a vector, suitably an expression vector adapted to promote transcription of the sequence in appropriate host cells. The selection of suitable vectors and methods of their preparation are well known to those skilled in the art and are described, for example, in Sambrook.

Transformation techniques for introducing the nucleotide sequence of the invention into host cells are well known to those skilled in the art and include such techniques as microinjection, high velocity, ballistic penetration and agrobacterium mediated transformation.

Conveniently, the nucleotide sequence of the invention may be introduced into the plant in such a manner as to effect reduction or suppression of PGM expression by sense or antisense suppression. Methods for achieving sense or antisense suppression are well known in the art. Conventionally, the nucleotide sequence to be introduced is operably linked to a promoter which allows transcription of the nucleotide sequence. Suitable promoters are known in the art and may be inducible, constitutive or tissue-specific, for example.

Introduction into the plant of a sequence according to the invention in the antisense orientation relative to the promoter will result in a reduction of the levels of expression. Sense suppression, wherein the presence of additional sense sequences inhibits the expression of the native gene is also well documented in plants (for example, see Matzke & Matzke, 1995 Plant Physiol, 107, 679–685). Antisense methods are thought to operate via the production of antisense mRNA which hybridises to the sense mRNA, preventing its translation into functional polypeptide. The exact mechanism of sense suppression is unclear but it too requires homology between the introduced sequence and the target gene. In the case of both antisense and sense suppression, neither a full length nucleotide sequence nor a "native" sequence is essential. Fragments of nucleotide sequence of various sizes may be functional in altering PGM levels and may be determined by those skilled in the art using comparatively simple trial and error.

Plants, particularly pea plants, having substantially reduced PGM(p) activity or substantially lacking PGM(p) activity are provided.

The invention also provides a method of altering one or more characteristics of a plant, or part thereof, particularly a pea plant, comprising altering the plant to reduce the PGM(p) activity in the plant. Suitably, the harvest window may be extended or the sucrose content increased.

The plant into which the sequence is introduced is preferably a commercially significant plant in which PGM performs a role and which is amenable to plant transformation techniques. Examples include carrot, tomato, peppers.

It will be appreciated that the method of extending the harvest window is of particular benefit when applied to pea plants in view of the particular practical difficulties attendent upon their short harvest window. The method may suitable be applied to any other plant where extending the harvest window is desirable, for example, green beans.

The invention also includes within its scope roots, seeds, fruit and other plant products of the plants of the invention.

Pea plants in accordance with the invention may be produced by producing a plant with the genotype rug3rug3.

The mutant pea SIM lines 1, 32, 41, 42 and 43 produced by the mutagenesis programme of Wang et al described above have this characteristic. However, these pea lines are not of generally acceptable agronomic character for commercial use, in terms of characteristics such as disease resistance, seed size, texture, plant height etc. For commercial use, new lines or varieties can be produced that are of acceptable agronomic character and include the rug3 mutation.

These can be produced by a conventional plant breeding approach, e.g. by crossing suitable SIM line plants with commercially acceptable varieties of which there are a large number, e.g. Novella, Bikini etc. Suitable plant breeding techniques are well known to those skilled in the art.

Another approach is to undertake a mutagenesis programme following the procedure of Wang et al as discussed above (as described in Plant Breeding 105, 311–320 (1990)) starting with a suitable commercial variety of pea plant (rather than a round seeded pea as Wang et al did) and to produce a rug3 mutant of the commercial variety. The desired mutants can be identified by testing starch levels in the seed or other plant parts.

An alternative approach is to use recombinant DNA technology to produce transformed plants in which PGM(p) gene expression is down regulated or inactivated at least in the developing pea seeds. Suitable techniques are known to those skilled in the art, e.g. as discussed in Davies et al Plant Cell Reports 12, 180–183 (1993). A review of the subject is given by D R Davies and P M Mullineau in Chapter 10 (Tissue Culture and Transformation) in Peas: Genetics, Molecular Biology and Biotechnology edited by R Casey and D R Davies, published by CAB International, 1993. See also U.S. Pat. No. 5,498,831, the content of which is incorporated herein by reference.

Suitable methods by which PGM gene expression may be down regulated or inactivated specifically in the developing pea seed include:

1) Tissue and temporal-specific down regulation of the PGM gene in developing peas via antisense or sense suppression technologies. This may be achieved by genetically transforming wild type Rug3Rug3 peas with transgene constructs comprising a pea seed-specific promoter (which mimics as closely as possible the seed expression profile of the native PGM gene) fused to parts of the coding region of the pea PGM gene in sense and antisense configurations. This is illustrated in FIG. 2.

Various sub-fragments of the pea PGM cDNA may be fused downstream of a pea seed specific promoter in both sense and antisense orientations. The promoter to be used will be chosen on the basis of being the one which most closely mimics, in activity, the expression pattern of native PGM within the developing pea. Such promoters may be derived from members of the vicillin gene family, the leghaemoglobin gene family, the phaseolin gene family, the USP (unidentified seed protein) gene or other suitable genes. A suitable 3' terminator/polyadenylation region (e.g. the nopaline synthase polyadenylation sequence) will also be fused downstream of the PGM sequences. These constructs will be built into the T-DNA region of a suitable Agrobacterium binary vector such as Bin19, pGPTV or a suitable RS76 derivative. If not already present, the BAR selectable marker gene encoding resistance to phophinothricin, or a suitable alternative, will also be introduced in the T-DNA. The constructs will be transformed into defined pea lines using standard pea transformation procedures, e.g. as developed at the John Innes Centre, Norwich. Transformants will be screened for the presence of single-low copy T-DNA insertions and the expression of the native PGM gene will be assayed at the RNA level and at the expressed protein level. Those displaying significantly reduced levels of PGM RNA and PGM protein or protein activity specifically within the developing pea will be taken for further analyses as candidates for the desired result.

2) Tissue and temporal-specific partial complimentation of rug3 material. In this case a full-length PGM cDNA clone (from pea, spinach or other available sources) will be fused to a promoter which specifies expression in a range of relevant tissues (leaves, stems, etc) but not the pertinent tissues of the developing pea seed (see FIG. 3). This will give rise to plants which retain the rug3 phenotype within the pea seed, but will be effectively wild type in other plant tissues. This means the other tissues such as stems, leaves etc are of normal sweetness and so are no more susceptible to predation than conventional plants.

The coding region of the PGM gene from pea, spinach or is another suitable source will be fused downstream of a promoter sequence which gives rise to no activity in developing pea seeds, but as close as possible to wild-type activity in other parts of the plant. A suitable polyadenylation/terminator sequence may be fused downstream of the PGM coding sequence. The gene construct may be built within the T-DNA of a suitable Agrobacterium transformation vector as described above. The transgene construct may be transformed into rug3 or rug3 derived material using standard methods as described above, but optimised for use with the rug3 material. Transformants with single to low copy number T-DNA integrations will be identified. Expression of the PGM transgenes may be assayed at the RNA level and for presence/absence of PGM protein or activity. Those lines in which PGM remains absent in the seed, but is present in other plant parts may be taken for further as candidates for the desired result.

The invention will be further described, by way of illustration, in the following detailed description and with reference to the accompanying Figures in which:

FIG. 1 shows the nucleotide sequence and deduced amino acid sequence for the pea PGM(p) cDNA clone (SEQ ID Nos. 3 and 4).

FIG. 2 illustrates schematically gene constructions for seed-specific down-regulation of PGM(p) activity; and FIG. 3 illustrates schematically gene construction for partial complementation of rug3.

Figure 7:
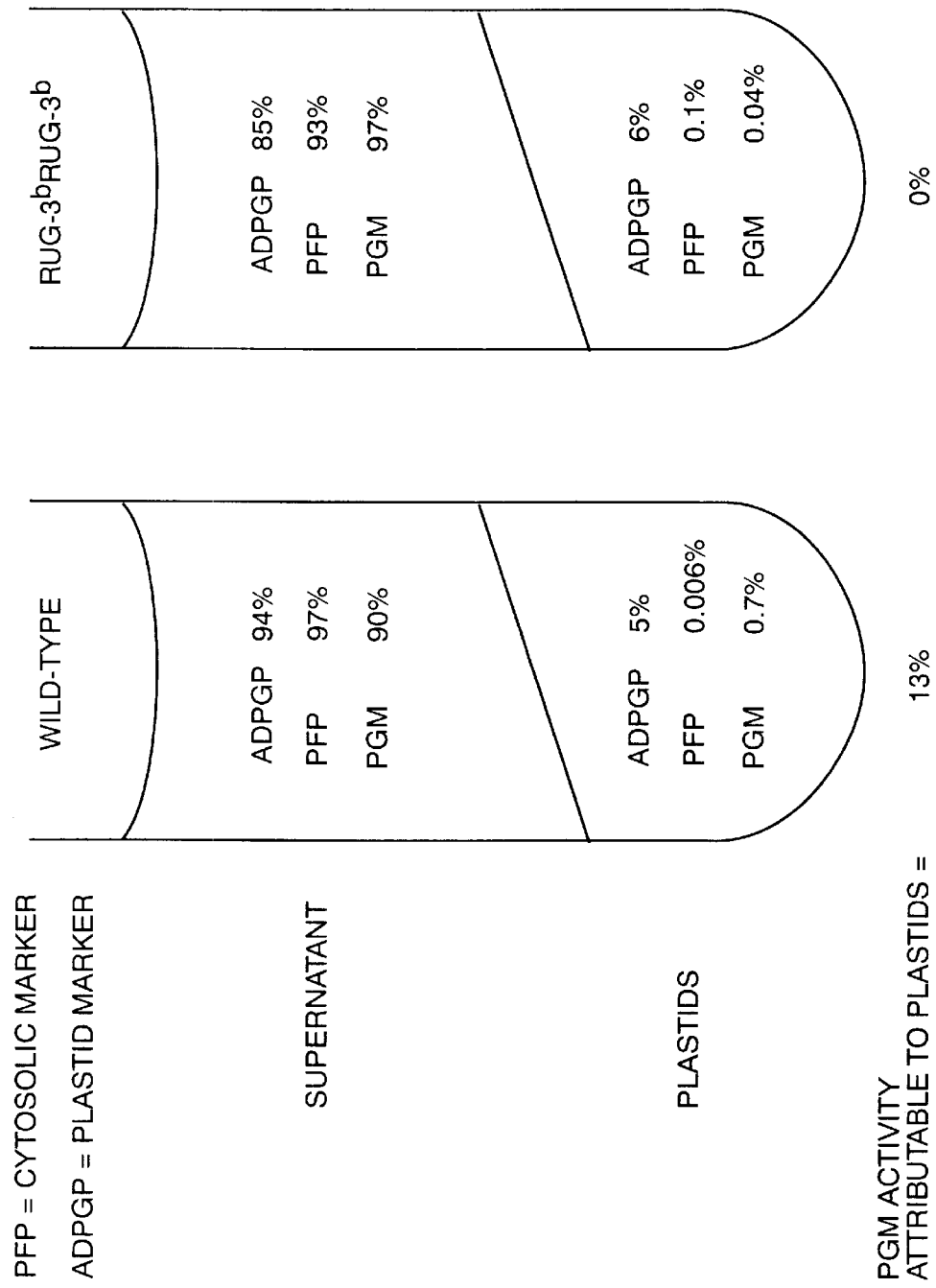
Figure 8:
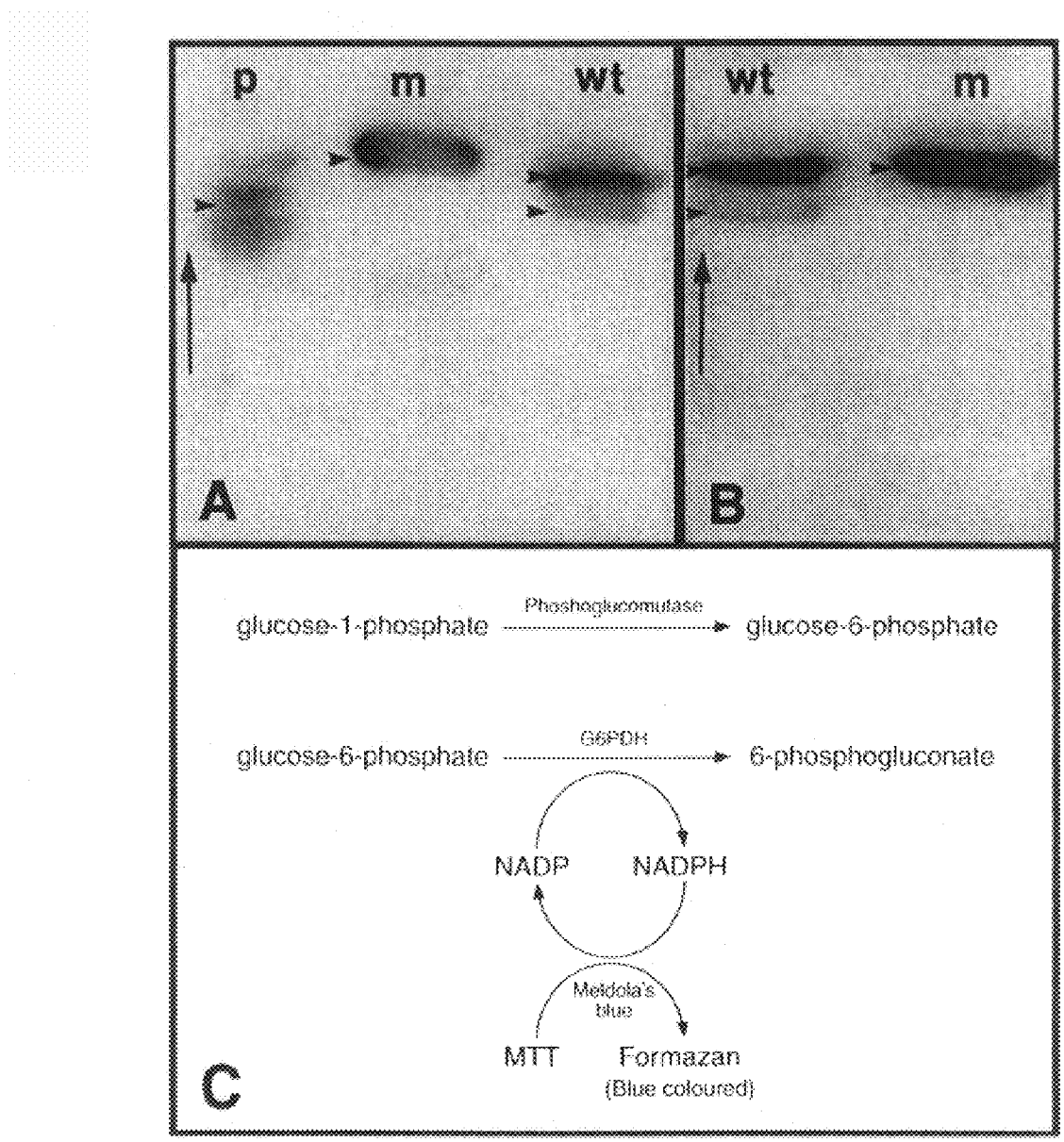

FIG. 7 is a diagrammatic representation of the method by which plastidial PGM activity was assayed. The values shown are the actual results from one pair of experiments. Calculations of the plastidial PGM activities were carried out as described. ADPGP=ADP glucose pyrophosphorylase. PGM=phosphoglucomutase. PFP=phosphate dependent fructose-6-phosphate 1-phosphotransferase;

FIG. 8 illustrates starch gel electrophoresis, comprising:

A) Zymogram showing PGM activity from (p) purified plastids from ca. 300 mg wild-type embryos, (m) extract from leaves of a rug3$^b$rug3$^b$ mutant plant, (wt) extract from wild-type leaves. The lower (less anodal) band in track (p) was enhanced relative to the upper band indicating that the lower band corresponds to the activity of plastidial PGM. The faint band present in track (m) lower (less anodal) than the major (arrowed) band was only seen in this experiment and may have been an artifact. The large arrow shows the direction of migration (towards the anode).

B) Zymogram comparing extracts from (wt) wild-type and (m) rug3$^b$rug3$^b$ mutant leaves. The electrophoresis of this gel was continued for a longer period than that shown in (A) and clearly showed the absence of the less anodal, plastidial PGM band in the mutant (m) track.

Figure 9:
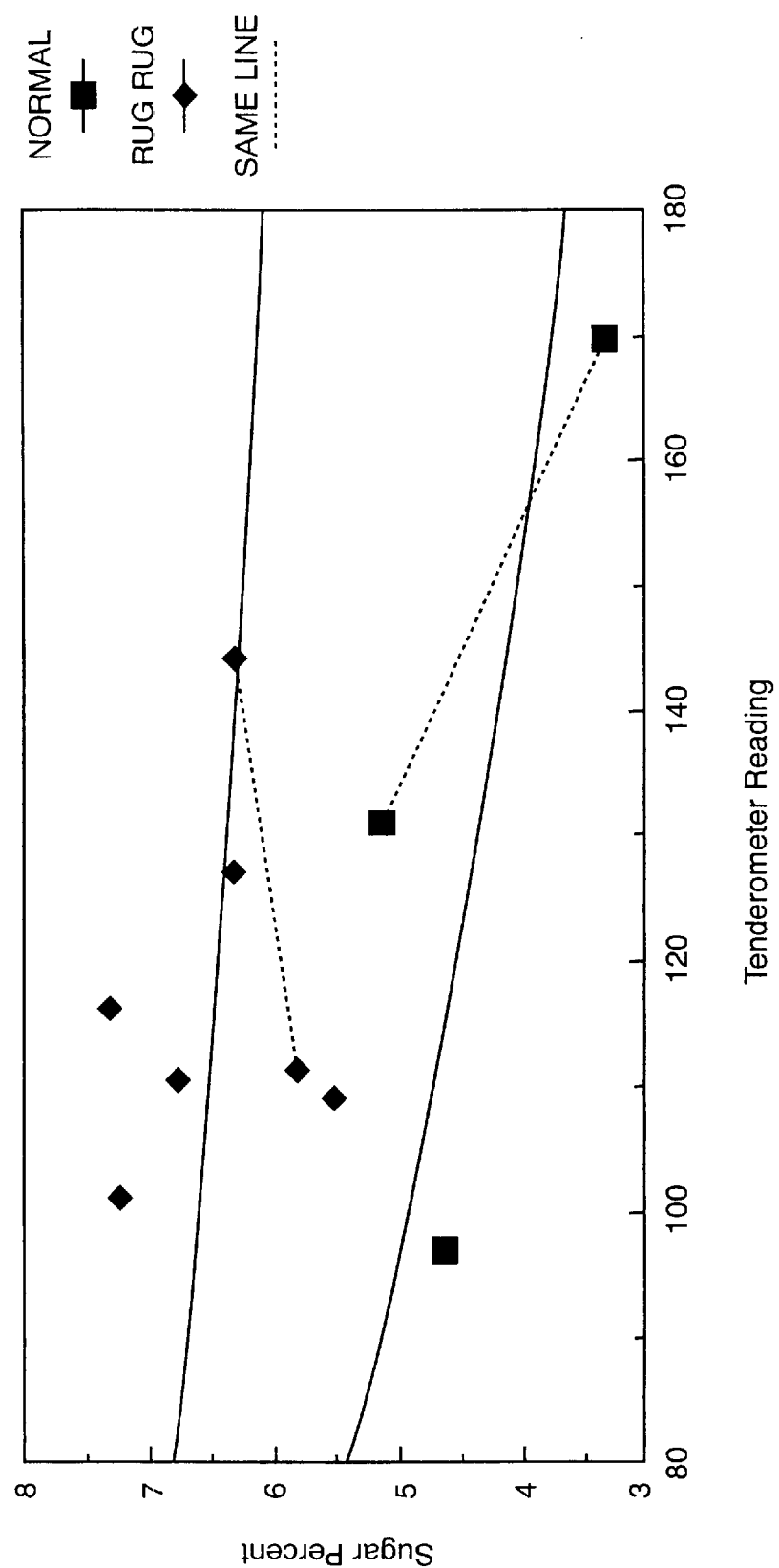

C) The reactions involved in the staining of the zymograms for PGM activity. MTT=2,5-diphenyltetrazolium bromide (thiazoyl blue);

FIG. 9 is a graph of relative sugar levels versus tenderometer readings, illustrating change in sugar content of peas with maturity. The diamonds represent the rug3 lines and the squares, the lines from the same crosses of similar agronomic performance that did not inherit the rug3 character. The dotted lines join samples taken from the same line at different maturities.

DETAILED DESCRIPTION OF THE INVENTION

A series of investigations were carried out on rug3 mutant peas resulting from the mutagenesis program of Wang et al described above.

Plant Material

Comparisons between plants of the genotype rug3rug3 and wild-type, round-seeded plants have been made. Experiments involving such comparisons have utilised near-isogenic pea lines, largely differing only with respect to the rug3 locus. These near-isolines were obtained by selfing and reselecting lines heterozygous at the rug3 locus for six generations. By this method, each wrinkled seeded (rug3rug3) line had its own corresponding round-seeded (Rug3Rug3 or ++) line.

Growth Conditions

Seeds of each of the rug3rug3 lines together with seeds near-isogenic to each line except for alleles at the rug3 locus were grown in the glasshouse. Glasshouses were maintained in a 15/10° C. day/night cycle with a minimum photoperiod of 16 hours. Several sowings were carried out in order to provide a continual supply of fresh leaf and embryo material and as necessary, plants were grown outdoors for the purpose of germination and growth trials. BC1 plants and $F_1$ and $F_2$ plants resulting from the crosses mentioned above were glasshouse grown.

For the purpose of comparing rug3rug3 plants with their wild-type near-isogenic partners throughout development, plants were randomised and grown in a controlled environment room (Weiss Technik, Reiskirchen, Germany) in John Innes No. 1 compost with 30% chick-grit. Plants were illuminated for 16 hours per day at an intensity of approximately 300 $\mu$E at plant level (HQI lamps; Wotan Powerstars, Osram, Wembley, UK) and the temperature maintained at 15° C. during the light period and 10° C. in the dark. The relative humidity was 75%.

Controlled Environment Experiments

The production of flowers on plants grown in controlled environment rooms was carefully monitored and the developmental stage corresponding to one day post-anthesis was deemed to be that time at which the outer petals of the flower had opened and were roughly perpendicular to the inner petals. At this stage, flowers were tagged and the date recorded. Flowers from the same node were removed. When three pods had begun to develop on a plant, the apex was removed in order to prevent further upward growth and as side shoots appeared on the plants, they too were removed. The three pods therefore were the only ones allowed to develop and in this way, competition for nutrients between pods was reduced.

For all developmental studies, pods were sampled at ten time points between 15 and 45 days after anthesis. After removal, pods and seeds were kept on ice and processed according to the specific experiment. In all cases, the three seeds most central in the pods were those sampled.

Growth Analysis

After harvesting pods at specific time points, the three seeds from each pod were weighed. The embryo was dissected from the testa and, after blotting away any liquid endosperm, the embryo and testa were weighed separately, both fresh and after freeze-drying.

Measurements of Sucrose Content of Seeds

Whole seeds were harvested throughout development and fresh weights recorded. The weights of the seeds ranged from approximately 20 mg to 600 mg from both wild-type and rug3rug3 plants. The seeds were freeze-dried and soluble sugars extracted by boiling in 5 ml 80% v/v ethanol followed by grinding to a fine paste. After pelleting the solids by centrifugation at 2000 g for 10 minutes, the supernatant was removed and evaporated to dryness. More 80% ethanol was added to the pellet and the process was repeated twice more. The supernatants from each stage were pooled and evaporated to dryness to leave a final pellet containing all of the soluble sugars. Extracts were analysed by ion chromatography under the following conditions:

Chromatograph: Dionex 4000i (BIO LC) I,d. (10 $\mu$m).

Column: Guard; CarboPac PA1 50 mm×4 mm Main; CarboPac PA1 250 mm×4 mm i,d. (10 $\mu$m).

Column temp. 25° C.

Injection vol. 25 $\mu$l

Mobile phase: 150 mM NaOH isocratic (continually degassed with He) at a flow of 1 ml/min.

Detector: Pulsed Amperometric (PAD), with gold working electrode and silver reference.

Detector settings: Range; 3 KnA

Applied Potentials; E1:+0.05V.(480 ms) E2:+0.60V.(120 ms) E3:−0.60V.(60 ms)

Assay of Enzyme Activities From Crude Extracts of Pea Embryos

Preparation of Crude Extracts

For measurement of total enzyme activities, 2 embryos (200–300 mg fresh weight) were extracted in 5–10 volumes of ice cold buffer containing 50 mM Mops (pH 7.2), 10% (v/v) ethanediol, 2 mM DTT. The embryos were ground with a pestle and mortar followed by an all glass homogeniser, and homogenates centrifuged at 10000 g at 4° C. for 10 minutes. The resulting supernatants, henceforth referred to as crude extracts, were placed on ice and assayed immediately.

Spectrophotometric Assays

All spectrophotometric assays were carried out in 1ml disposable plastic cuvettes at 25° C. and monitored using a Phillips PU 8800 spectrophotometer. Each reaction mixture is given below, with the reference from which they were modified given in parentheses. All coupling enzymes in the reactions were supplied by Boehringer Mannheim.

ADPglucose pyrophosphorylase (EC 2.7.7.27; Hill and Smith, Planta 185, 91, 1991)

The assay was carried out in 80 mM Hepes (pH 7.9 buffer containing 1.5 mM sodium pyrophosphate, 5 mM $MgCl_2$, 0.8 mM NAD, 2 mM ADPglucose, 5 units of glucose 6-phosphate dehydrogenase (NAD-linked, from Leuconostoc mesenteroides), 2 of units phosphoglucomutase and 10 to 50 µl of crude extract. All components of the reaction mixture except for sodium pyrophosphate were combined in a 1 ml disposable cuvette and the reaction monitored spectrophotometrically at 340 nm. When a steady basal reaction rate was achieved, the sodium pyrophosphate was added to the reaction mixture, the cuvette returned to the spectrophotometer and the assay reaction rate determined.

UDPglucose pyrophosphorylase (EC 2.7.7.9; Smith et al, Plant Physiology 89, 1279–1284, 1989)

The assay was carried out in 80 mM Bicine (pH 8.6) buffer containing 1.5 mM sodium pyrophosphate, 1 mM $MgCl_2$, 0.8 mM NAD, 0.8 mM UDP glucose, 10 units of glucose-6-phosphate dehydrogenase (NAD-linked, from Leuconostoc mesenteroides), 4 units of phosphoglucomutase and 10 to 50 µl of a two-fold dilution of crude extract. The basal and assay reaction rates were determined as for ADPglucose pyrophosphorylase except that the reaction was initiated with UDPglucose.

Phosphoglucomutase (EC 2.7.5.5; Foster and Smith, Planta 190, 17–24, 1993)

The assay was carried out in 50 mM Bicine (pH 8.5) buffer containing 0.8 mM NAD, 1 mM $MgCl_2$, 6 mM glucose 1-phosphate, 2 units of glucose 6-phosphate dehydrogenase (NAD-linked, from Leuconostoc mesenteroides) and 10 to 50 µl of crude extract. The basal and assay reaction rates were determined as for ADPglucose pyrophosphorylase except that the reaction was initiated with glucose-1-phosphate.

Radiometric Assay for ADPglucose Soluble Starch Synthase

This assay, modified from Smith et al Plant Physiology 89, 1279–1284 (1989) contained in 200 µl 100 mM Bicine (pH 8.5), 5 mM EDTA, 25 mM potassium acetate, 10 mM DTT, 1 mM ADPglucose, amylopectin (5 mg $ml^{-1}$), 0.23 KBq ADP[U-$^{14}$C] glucose and 20 µl of crude extract. The reaction was initiated with the crude extract and incubated at 25° C. for precisely 10 minutes after which time the reaction was stopped by boiling for 1 minute. Glucose polymer was precipitated with 3 ml 75% methanol, 1% KCl (v/v). Blanks were included which had been incubated at 100° C. immediately after addition of the crude extract. Radioactivity incorporated into glucose polymer was determined by liquid scintillation spectrometry using Optiphase HiSafe II scintillant (LKB Scintillation Products, Loughborough, England) in a LKB 1219 Rackbeta scintillation counter.

Assays of Amyloplast Enzyme Activities

Amyloplast Isolation

Isolation of amyloplasts was carried out by a method adapted from Hill and Smith, Planta 185,91 (1991), Smith et al. Planta 180, 517–523 (1990) and Denyer and Smith, Planta 173, 172–182 (1988).

Extraction medium (medium A) was prepared according to Hill and Smith (1991) referred to above and contained 500 mM sorbitol, 20 mM Hepes (pH 7.4), 10 mM KCl, 1mM $MgCl_2$, 1mM EDTA, 5 mM DTT, 10% (v/v) ethanediol, 1% (w/v) BSA. Approximately 5 g of embryos of individual masses around 200 mg from either rug3 mutant plants or their equivalent wild-type isoline were chopped with razor blades in medium A. The extract was removed and replaced with fresh medium 3–4 times giving a known total volume of extract (15–20 ml). The extract was filtered through two layers of Miracloth (Chicopee Mills, N.J., USA) into 30 ml Corex tubes (Corning glass works) on ice and 1 ml removed for assaying total enzyme activity. The remaining filtrate was centrifuged in a slow speed centrifuge at approximately 30 g. The resulting supernatant was retained for assay, the pellet was resuspended in 10 ml of medium A and centrifuged as before. The final pellet containing washed amyloplasts was resuspended in 0.5 ml medium A. Complete lysis of intact amyloplasts in each fraction was achieved by vortexing for 30 seconds followed by vigorous expulsion through a hypodermic syringe needle. Extracts from all fractions were centrifuged at 10000 g for 10 minutes to remove solids.

Enzyme Assays of Amyloplast Preparations

After the isolation of amyloplasts as described above, phosphoglucomutase activity and marker enzyme activity for amyloplasts and cytosol were assayed in all fractions.

Marker enzyme activities were activities normally associated with specific compartments of the plant cell. For the amyloplasts, the marker enzymes were ADPglucose pyrophosphorylase and glyceraldehyde-3-phosphate dehydrogenase (GAPDH; EC 1.2.1.12), and for the cytosol, pyrophosphate-dependent fructose-6-phosphate 1-phosphotransferase (PFP; EC 9.7.1.90) and alcohol dehydrogenase (ADH; BC 1.1.1.1).

ADPglucose pyrophosphorylase activity was assayed as in crude embryo extracts except that crude extract was replaced in the assay mixture by the appropriate fraction from the amyloplast preparation.

The assay for GAPDH activity was modified from Wu and Racker, The Journal of Biological Chemistry 234, 1029–1035 (1958) and contained in 1 ml: 80 mM Mops (pH 7.4), 9 mM $MgCl_2$, 3 mM ATP, 0.2 mM NADPH, 5 mM 3-phosphoglyceric acid (3-PGA), 2.5 of units 3-phosphoglycerate kinase and 10–50 µl of the appropriate fraction resulting from the amyloplast preparation. The reaction was initiated with 3-PGA and monitored spectrophotometrically at 340 nm.

PFP was assayed by a method modified from Smith, Planta 166, 264–270 (1985). The assay contained in 1: 70 mM Mops (pH 7.5), 1.5 mM $MgCl_2$, 10 mM fructose-6-phosphate, 1.5 mM sodium pyrophosphate, 0.015 mM fructose-2,6-bisphosphate, 0.18 mM NADH, 10 units of triose phosphate isomerase, 0.1 unit of aldolase, 1 unit of glycerol-3-phosphate dehydrogenase and 50 µl of the appropriate fraction resulting from the amyloplast preparation. The reaction was initiated with sodium pyrophosphate and monitored spectrophotometrically at 340 nm.

The assay for ADH activity contained in 1 ml: 75 mM glycylglycine (pH 9.0), 100 mM ethanol, 0.8 mM NAD and 10–50 µl of the appropriate fraction from the amyloplast preparation. The reaction was initiated with ethanol and monitored spectrophotometrically at 340 nm.

Phosphoglucomutase activity was assayed as in crude embryo extracts except that crude extract was replaced in the assay mixture by the appropriate fraction from the amyloplast preparation.

The proportions of phosphoglucomutase activity attributable to the cytosol and plastids were calculated using the following equations:

$$P+C=T \quad (1)$$

where P is plastidial PGM activity, C is cytosolic PGM activity and T is total PGM activity in an embryo extract; and $$(M_c\%\times C)+(M_p\%\times P)=P_a$$

where $M_c$ is cytosolic marker activity, $M_p$ is plastidial marker activity and $P_a$ is the PGM activity assayed in the plastid fraction resulting from the isolation described above, i.e.

$$M_c C + M_p P = 100 P_a \quad (2).$$

Substituting the values for $M_c$, $M_P$ and $P_a$ obtained from the assays into the equation and solving equations (1) and (2) simultaneously gives the values for P and C.

Starch Gel Electrophoresis

Buffers for starch gel electrophoresis were prepared according to Selander et al, Biochemical polymorphism and systematics in the genus Peromyscus. I. Variation in the old-field mouse (*Peromyscus polionotus*). University of Texas Publications 7103, 49–90. (1971). The electrode buffer was lithium-borate, pH 8.1 (0.03M lithium hydroxide, 0.19M boric acid). The gel buffer was comprised of 1 part electrode buffer and 9 parts tris-citrate buffer, pH 8.4 (0.05M tris, 0.008M citric acid). Extraction buffer consisted of 0.05M Tris-HCl, pH 8, 2 mM DTT.

Starch gels were prepared by suspending 11.25 g potato starch (hydrolysed for electrophoresis; Sigma-Aldrich company, Dorset, England) in 150 ml gel buffer. The suspension was heated in a 250 ml side-arm flask with stirring until the mixture boiled and became transparent. At this point, the flask was sealed with a rubber bung and the gel de-gassed by attaching a vacuum line to the side arm of the flask. The gel was then poured immediately into a former and covered loosely. After becoming solid at room temperature, the gel was then cooled overnight to 4° C.

Samples for electrophoresis were prepared by grinding leaves and embryos from wild-type and rug3rug3 plants in a minimum amount of extraction buffer so that a thick slurry was produced. The extract was then allowed to soak into filter paper wicks (Whatman No.182) for approximately 10 minutes at 4° C. When fully impregnated, the wicks were inserted into a slit made 2 cm from the cathodal edge of the gel.

Electrophoresis of the starch gel was carried out at 300v and 4° C. The surface of the gel was covered with a sheet of polythene and in some experiments additional cooling was provided as suggested by Przybylska et al, Genetica Polonica 30, 120–138 (1989) by placing a bag of ice on top of the polythene sheet. After approximately 30 minutes, the current was switched off and the paper wicks were removed from the gel. Electrophoresis was then continued for a further 6 hours. After this period, gels were removed from the electrophoresis apparatus and laid on a flat surface. Horizontal slices were made through the gel using a taught 0.008" diameter guitar string. Slicing in this way was necessary to remove the top surface of the starch gel which formed a skin which did not have the matrix properties of the centre of the gel. Internal slices from the gel were laid in a shallow dish and staining solution poured over the surface.

Staining for PGM activity was achieved by a method adapted from Thorpe et al, Procedures for the detection of isozymes of Rapeseed by starch gel electrophoresis. Department of crop science technical bulletin Agriculture Canada. (1987). The stain consisted of 50 ml 0.1M Tris-Histidine buffer (pH8; 0.1M tris titrated to correct pH with histidine-HCl) containing 100 mg $MgCl_2$, 120 mg glucose-1-phosphate, 10 mg NADP, 20 mg thiazoyl blue (MTT), a trace of 8-dimethylamino-2,3-benzophenoxazine (Meldola's blue) and 50 units of glucose-6-phosphate dehydrogenase (from Leuconostoc mesenteroides).

The starch gel was immersed in stain for 60 minutes at 37° C. in darkness. Violet bands of enzyme activity were easily visible after this time.

Analysis of Sugars in Developing Seeds

To analyse the sugar content of rug3rug3 and wild-type seeds throughout development, plants were grown under controlled conditions as described above. $rug3^a rug3^a$ seeds and their corresponding wild-type isoline were used in these experiments. Pea seeds were harvested to give 10 or 11 time points in the range between 15 and 45 days after anthesis. For each time point, two pods were harvested and three seeds analysed from each pod. The measurements recorded for each time point were the fresh and dry weights of the seeds.

Figure 4:
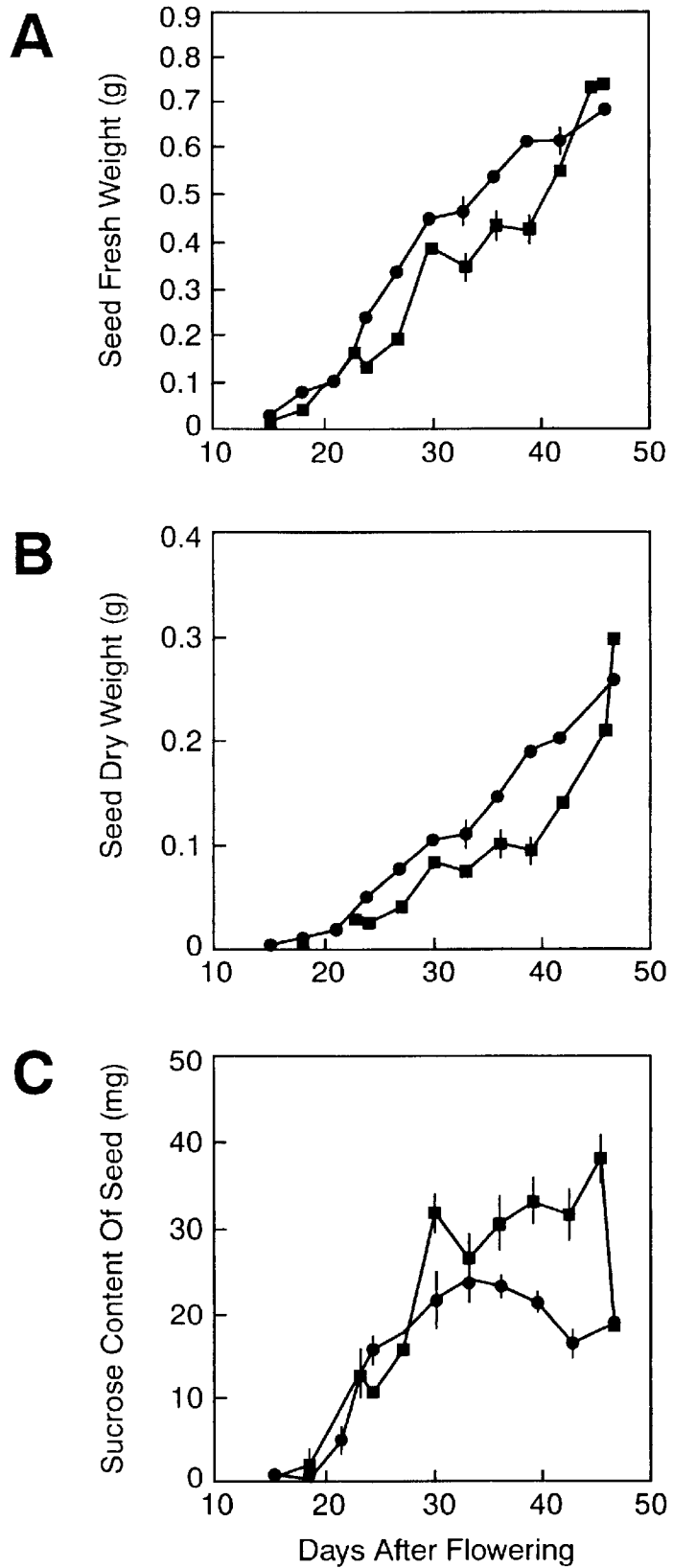
FIG. 4 is a series of graphs showing changes in (a) seed fresh weight, (b) seed dry weight, (c) sucrose content of the seed, with time (number of days after flowering) for the rug3$^a$rug3$^a$ line (squares) and its wild-type near isoline (circles)
Figure 5:
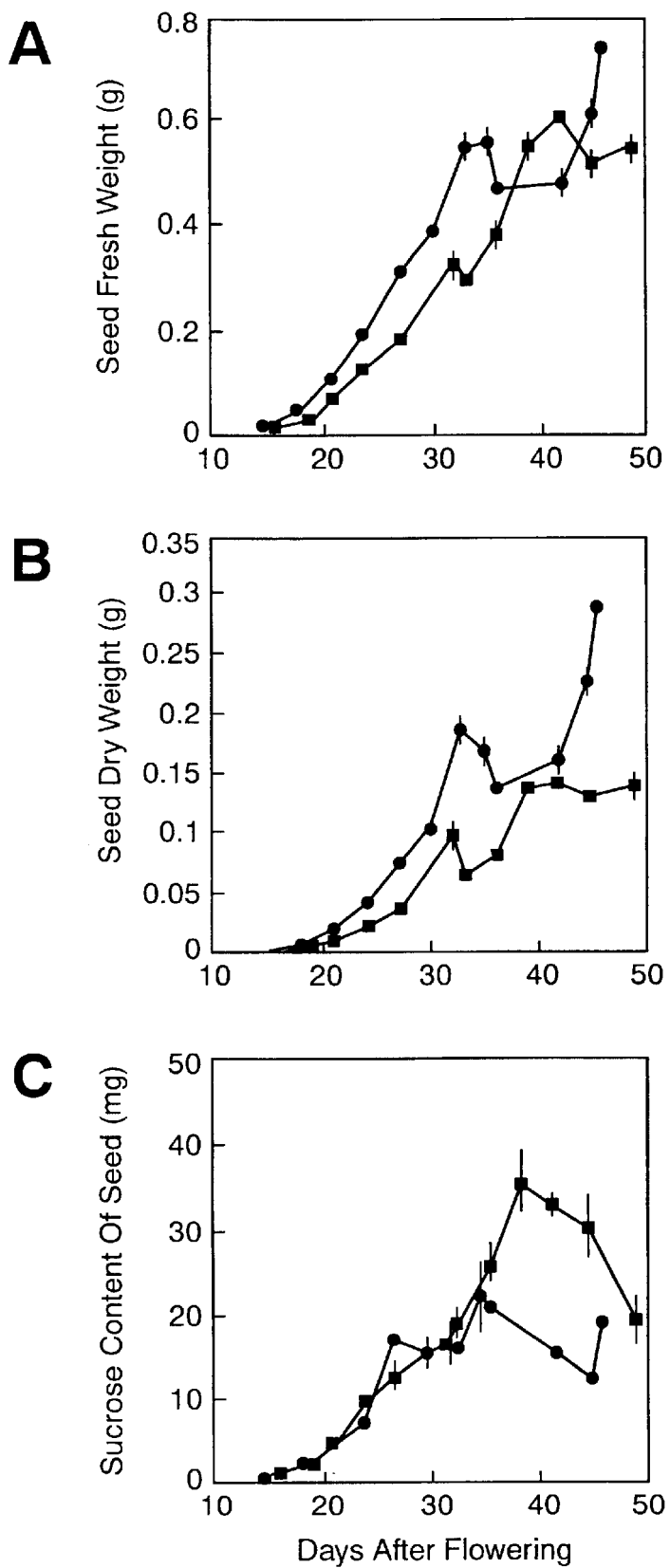
FIG. 5 is a series of graphs showing changes in (a) seed fresh weight, (b) seed dry weight, (c) sucrose content of the seed, with time (number of days after flowering) for the rug3$^b$rug3$^b$ line (squares) and its wild-type near isoline (circles)

FIGS. 4 and 5 shows the data represented as means for each time point with standard errors for the two near-isogenic pairs investigated. In the $rug3^a rug3^a$ mutant and wild-type near-isoline, the absolute levels of sucrose in the seed are not significantly different until approximately 30 DAF.

After this time, significant differences exist as the mutant seeds continue to accumulate sucrose until 45 DAF, whilst the wild-type seeds showed a decrease in the sucrose content from 30 DAF onwards. At 45 DAF, the value for the mutant seed falls to a level not significantly different to that of the wild-type. In the $rug3^b rug3^b$ mutant and the corresponding near-isogenic wild-type seeds significant differences in the sucrose content of the seeds do not occur until after approximately 35 DAF. The mutant seeds continued to accumulate sucrose until 40 DAF when a decline in the content was observed, whilst in the wild-type seeds, the sucrose content fell between 35 DAF and 40 DAF. An unexpected increase in the sucrose content of the wild-type seeds was observed after 40 DAF, however, this growth curve of this wild-type line was unusual at around the 40 DAF time point and may reflect problems which occurred with the growth of these plants. The errors associated with measurements made on the seeds of this line in this experiment are greater than those of the other lines and this is probably also attributable to growing problems.

A feature of the pattern of sucrose accumulation of both mutant lines was the rapid decline in the sucrose content of the seeds towards the end of development, such that differences in sucrose content between wild-type and mutant seeds became less significant. The fresh and dry weight curves also shown in FIGS. 4 and 5 (a and b) serve to demonstrate that the seeds of all lines investigated have not begun to dry off at the 45 DAF stage and it is therefore possible that the values for sucrose content would again diverge after this time, giving rise to differences in sucrose content of mature wild-type and rug3rug3 seeds. These values are 7% and 3% of the dry weight of mutant and wild-type seeds respectively and cannot merely be accounted for by differences in seed final dry weights. That is to say that they reflect an increased absolute quantity of sucrose in rug3rug3 seeds.

Measurement of Enzyme Specific Activities in Developing Embryos

Figure 6:
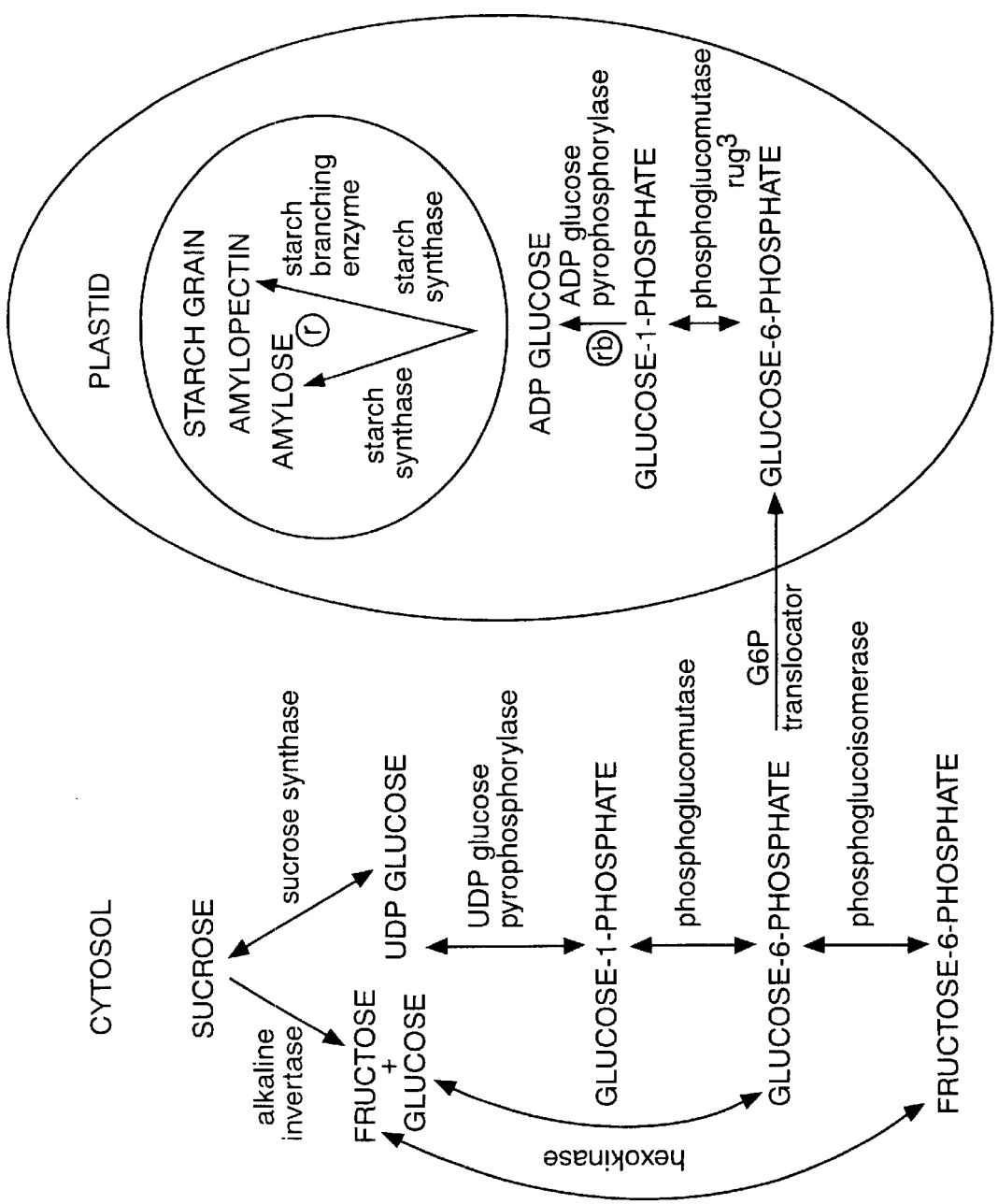
FIG. 6 shows the pathway of starch synthesis in pea embryos, indicating activities affected by the mutations at the rugosus loci (r, rb and rug3)

The r and rb mutants in pea both affect enzymes in the starch biosynthetic pathway as shown in FIG. 6 and, as a result of the consequent reduction in starch content, lead to wrinkling of the mature seed. By direct analogy to these mutants, the most likely effect of the rug3 mutation would seem also to be on the activity of an enzyme in this pathway. This does not mean however that the enzyme or enzymes need to be affected directly, the mutation may produce changes in regulatory mechanisms of the pathway. Additional evidence for rug3 affecting starch biosynthetic enzymes comes from the existing starchless mutants of other is plants. In these cases the mutations are known to affect the activity of either ADPglucose pyrophosphorylase or plastidial phosphoglucomutase.

The activities of the enzymes of the starch biosynthetic pathway have been assayed, therefore, in extracts from both rug3 mutant embryos and their near-isogenic wild-type equivalents. Embryos were analysed from rug3rug3 plants representing the extremes of the allelic series in terms of starch content of the mature seeds, i.e. those bearing the rug3$^a$ and rug3$^b$ alleles. For the purposes of making these measurements, embryos were harvested at between 200 and 300 mg fresh weight, which is a developmental stage when starch synthesis would be expected to be occurring at a rapid rate, and hence at a stage when the enzymes of the pathway should be most active (Smith et al, Plant Physiology 107, 673–678, 1989). The enzymes chosen for assay in the first instance were: UDPglucose pyrophosphorylase, phosphoglucomutase (PGM; total activity), phosphoglucomutase (plastidal isoform; PGM(p), ADPglucose pyrophosphorylase and starch synthase. These enzymes were chosen to be assayed for the following reasons. Firstly, they are the main enzymes involved in starch synthesis. Secondly, they catalyse reactions which (as far as is known) cannot be carried out via alternative routes. The activity of some of them is known to be affected in starch mutants of pea and other plants. Finally they can be assayed by established techniques. The major omission from this round of experiments was the measurement of the glucose-6-phosphate (G-6-P) translocator which is responsible for the movement of G-6-P from the cytosol into the amyloplasts. The assay of this activity is not straightforward and it was considered that measurements could be carried out at a later date should it prove necessary. In addition, since the rug3 mutations cause absence of starch from the leaves, and the substrates for starch synthesis are likely to be able to enter the leaf chloroplasts via different routes since they do not possess a G-6-P translocator, then it would seem unlikely that the primary effect of the mutation was on this molecule. Because of the severe effects of the rug3 mutation on starch synthesis, the aim of the investigations of enzyme specific activities was to identify activities which were severely reduced and could therefore account for the near-starchless phenotype of rug3rug3 plants.

The results of the assays of the aforementioned enzymes are shown in the following Table 3. The results of the assays of wild-type embryos, near isogenic to each of the rug3 mutant embryos used are comparable to those reported elsewhere (Smith et al, 1989 referred to above; Foster and Smith, Planta 190, 17–24, 1993). The single measurements obtained for the activity of starch synthase was due to the nature and cost of the radiometric assay involved. The initial data that was obtained clearly showed the presence of the activity of this enzyme in extracts from rug3 mutant embryos and hence the assay was not repeated. Differences in the apparent activity of starch synthase in the wild-type and mutant embryos may have been due to the embryos being of a different developmental stage despite similar fresh weights as discussed below. Alternatively, they may reflect real differences, possibly caused by up-regulation of the enzyme production in the rug3 embryos as a result of altered flux through the pathway.

Table 3

Results of the assays of enzyme activities from crude extracts and plastid preparations from 200–300 mg embryos. Units of enzyme activity shown are $\mu mol^{-1}\ min^{-1}\ g^{-1}$ fresh weight except for the activity of plastidial PGM which was calculated as a percentage of the total PGM activity. Figures are means of five assays from separate extracts+standard errors. ND=no activity detected.

TABLE 3

| Genotype of embryos | UDPGPP | Total PGM | Plastidial PGM | ADP glucose PP | Starch synthase |
| --- | --- | --- | --- | --- | --- |
| Rug3Rug3 | 5.29 ± 0.56 | 9.51 ± 0.83 | 11.6% ± 0.8 | 0.69 ± 0.07 | 0.49 |
| rug3$^a$rug3$^a$ | 3.55 ± 0.13 | 9.2 ± 1.82 | ND | 1.15 ± 0.31 | 0.86 |

Only one of the enzymes assayed was severely reduced in the extracts from rug3rug3 embryos and this was the plastidial isoform of phosphoglucomutase. No activity was attributed to the plastidial isoform of this enzyme from the rug3rug3 embryos even though substantial amounts of total PGM activity were present. The method by which the activity of the plastidial isoform of this enzyme was assessed was to purify plastids, and measure the amounts of marker enzymes for the plastids (ADPglucose pyrophosphorylase) and the cytosolic fraction (PFP or ADH), as described above. These enzymes were assayed along with PGM in all fractions obtained from the purification i.e. the plastid fraction, the total extract and the remainder left after removal of intact plastids. The presence of the plastid marker in the plastid fraction coupled with the absence of the cytosolic marker would indicate that pure plastids had been obtained. The recovery of the plastidial marker enzyme and the actual amount of contaminating cytosolic marker could be used to assess the yield and purity of the plastids. Assays of PGM were only carried out on extracts where a substantial proportion of the plastidial marker enzyme was recovered in the plastid fraction and hence the yield of plastids was high. Obviously the mechanical forces used in the extraction procedure would result in large numbers of the plastids being broken but 10% of the plastidial marker activity could be routinely recovered in the plastid traction. This recovery value was in agreement with that of Foster and Smith Planta 190, 17–24 (1993), who estimated the proportion of PGM activity which was attributable to the plastids of pea embryos to be approximately 20%. The diagram shown in FIG. 7 shows the method by which the PGM(p) activity was assessed and the actual recovery and assay results for one pair of experiments carried out concurrently. Fuller results of more extensive tests are given in Table 4.

Table 4

Enzyme specific activities measured in fractions resulting from plastid preparation. Activities shown are μmol min⁻¹g⁻¹ fresh weight or precentages±standard errors for two independent preparations. * represents the precentage activity assumed to be present in the plastids for the cytosolic and plastidial marker enzymes. † represents the activities of phosphoglucomutase in the plastids calculated as described above.

possible that real differences do exist in the activities of some of the important enzymes of the pathway. These might be accounted for by regulation of their activity through alterations to substrate concentrations in the mutant embryos. One such candidate for this type of regulation is ADPglucose pyrophosphorylase which, in the experiments reported here, had consistently higher activities in extracts from mutant embryos than from wild-type embryos. The substrate for this enzyme (G-1-P) would be practically

TABLE 4

| Plant type | Total activity | Activity in supernatant | Activity in plastids | % activity in supernatant | % activity in plastids | % recovery | % activity attributable to plastids |
|---|---|---|---|---|---|---|---|
| ADP glucose pyrophosphorylase | | | | | | | |
| WT | 0.184 ± 0.048 | 0.176 ± 0.058 | 0.012 ± 0.0005 | 93.6 ± 6.8 | 7.0 ± 1.5 | 100.6 ± 5.3 | 100* |
| Mutant | 0.578 ± 0.029 | 0.481 ± 0.033 | 0.065 ± 0.0051 | 83.2 ± 1.4 | 11.2 ± 1.3 | 94.4 ± 1.7 | 100* |
| Pyrophosphate dependent fructose-6-phosphate 1-phosphotransferase | | | | | | | |
| WT | 0.711 ± 0.324 | 0.728 ± 0.353 | 0.0007 ± 0 | 100.55 ± 3.9 | 0.12 ± 0.06 | 100.7 ± 3.8 | 0* |
| Mutant | 1.11 ± 0.09 | 0.988 ± 0.043 | 0.002 ± 0.001 | 89.7 ± 3.7 | 0.2 ± 0.1 | 89.9 ± 3.8 | 0* |
| Phosphoglucomutase | | | | | | | |
| WT | 6.595 ± 2.77 | 6.375 ± 2.6 | 0.053 ± 0.017 | 97.2 ± 1.2 | 0.84 ± 0.1 | 98.0 ± 1.34 | 10.6 ± 1.01 |
| Mutant | 7.532 ± 0.5 | 7.322 ± 0.47 | 0.007 ± 0.001 | 97.2 ± 0.2 | 0.09 ± 0.02 | 97.3 ± 0.02 | −0.8 ± 0.51 |

Numerous repetitions of the measurement of plastidial PGM could not reveal any activity of this enzyme in $rug3^b rug3^b$ embryos. In addition, no activity could be detected in the embryos of $rug3^a rug3^a$ plants using this technique, despite the accumulation of small amounts of starch in the seeds of this mutant. This perhaps suggests that the assay was not sensitive enough to detect small amounts of PGM(p) activity which may be present in $rug3^a rug3^a$ embryos.

The enzyme activities of all of the enzymes in the pathway of starch biosynthesis which were assayed except for PGM(p) showed little difference between rug3rug3 and wild-type embryos. The limited number of repetitions of the measurements meant that, with the exception of PGM(p) activity, these differences were not significant with 95% confidence limits (for UDPGPP, t=3.0, P>0.05; for ADPGPP. t=1.47, P>0.2; for PGM[total], t=0.26, P>0.5). It also must be considered that to cause the near-starchless phenotype of rug3rug3 seeds, a particular enzyme activity would have to be dramatically reduced in the starch synthesising tissues and this was only the case for PGM(p). Mutants at the rb locus have been shown to have a ten-fold decrease in the activity of ADPglucose pyrophosphorylase relative to the wild-type in 200–300 mg embryos and despite this, rbrb seeds contain 32% starch at maturity. As mentioned with reference to the single measurements of starch synthase above, differences in enzyme activities measured here may be attributable to the fact that rug3rug3 and wild-type embryos grew differently. Hence, although of approximately the same fresh weight, the increased water uptake in the mutant meant that the wild-type and mutant embryos were at different developmental stages. Further, it has been shown that a rug3rug3 embryo is likely to have a lower dry weight for a given fresh weight than a wild-type embryo. When these experiments were carried out, the growth data linking fresh and dry weight through development was not available for the rug3rug3 plants and therefore equal fresh weights were used as an estimate of equivalence in developmental stage between wild-type and mutant. It is absent from rug3rug3 plastids without the activity of PGM (p) and perhaps this results in up-regulation of the activity of the enzyme.

Overall, these experiments gave an indication that the activity of plastidial PGM was severely reduced in rug3rug3 embryos. The indirect method by which this enzyme is assayed, i.e. involving a calculation of the proportion of activity attributable to the plastids, prompted the need for other lines of evidence to support the initial findings.

Starch Gel Electrophoresis

The technique of starch gel electrophoresis has been used to separate isoforms of phosphoglucomutase (and many other enzymes) from pea for the purposes of genetic (isozyme) mapping (Weeden, The Journal of Heredity 75, 365–370, 1984 and 78, 153–159, 1987). The technique separates enzymes on the basis of charge and size and can reveal electrophoretic variance for the same enzyme between different plant lines. Crosses can be carried out between peas showing variation of this nature for a particular enzyme and the $F_2$ population analysed for the isozyme patterns which will correspond either to chat of one of the parents or to a combination of both parental patterns in the case of a heterozygote. The visualisation of enzymes on gels is carried out by means of a coupled reaction which takes place in the gel to yield a coloured product. FIG. 8C shows the reaction involved. The extensive use of this technique in pea meant that information was available regarding the migration of PGM isoforms on these gels (Przybylska et al, 1989 referred to above).

For practical reasons, namely obtaining extracts with sufficient concentrations of enzyme activity, leaves were used to provide samples for electrophoresis. This was not considered to be a problem as the rug3 mutation was known to affect the leaves, and in pea only two loci encoding the isoforms of phosphoglucomutase (one cytosolic and one plastidial) have been reported (Weeder and Marx, The Journal of Heredity 75, 365–370, 1984; Weeden et al, The Journal of Heredity 75, 411–412, 1984; and Przybylska et al, 1989 referred to above) The methods of starch gel electrophoresis presented several practical problems. Firstly, as the method has largely been superseded by isoelectric focusing using acrylamide gels for the purposes of genetic mapping, purpose built electrophoresis equipment was not available. Hence, equipment designed for the electrophoresis of nucleic acids in agarose gels was modified for the purpose. Problems also arose with the staining of the gels. Initially, no bands of enzyme activity could be seen on the gels when they were stained by the method of (Thorpe et al, 1987 referred to above). A method of N. F. Weeden was eventually employed. Przybylska et al (1989) referred to above reported that a migration of 10 cm of the front was necessary to separate the isoforms of PGM from pea in a 6% gel. This was also taken into consideration in later experiments.

FIG. 8B shows the results of a zymogram loaded with extracts from rug3$^b$rug3$^b$ leaves and the relevant wild-type isoline. The result appeared to confirm the absence of one isoform of PGM in the rug3rug3 extract. Results from Przybylska et al (1989) referred to above using the same buffer system as employed in these experiments (Lithium borate/triscitrate) report that the more anodal isoform of PGM in pea is the plastidial form, i.e. this form will migrate further towards the anode in these conditions. In the zymograms shown in FIG. 8 it is the anodal form which is absent from the rug3rug3 extract. An attempt was made to demonstrate that the anodal band was caused by PGM activity in the plastids. The method which had been used for the measurement of specific activities in plastids was used on a larger scale to attempt to isolate a sufficiently large extract from plastids from wild-type embryos to load onto a starch gel. The zymogram shown in FIG. 8A is the result of this experiment. It can be seen that the anodal band has been enhanced relevant to the cathodal band in the same track for the purified plastid sample. However, a smear was present more anodal than the plastidial PGM band. This could be due to starch in the plastid extract interfering with the matrix of the gel, or possibly components of the amyloplast isolation medium affecting the migration.

The results of the starch gel experiments along with the measurements of enzyme specific activities gave strong evidence that in rug3rug3 plants, the activity of the enzyme plastidial phosphoglucomutase was reduced to a level not detectable by these methods. Using leaves from rug3$^a$rug3$^a$ plants as the starting material for starch gel electrophoresis, no activity of the plastidial isoform of PGM could be seen after staining. A small amount of PGM(p) activity must have been present in this tissue to account for the small amount of starch synthesised in rug3$^a$rug3$^a$ embryos. However, it is likely that this residual activity was at an extremely low level as the embryos only accumulated approximately 20% of the starch of the wild type by the end of development. The activity of PGM(p) in these embryos may be so low that the methods used here are not sensitive enough to detect it. Also worthy of note is the fact that the activity of PGM on the whole is likely to be lower in leaf tissue than in embryos which are rapidly synthesising starch.

Breeding Programme

The rug3 mutant SIM lines used in the above work, while useful for experimental purposes, are not suitable for commercial use. A breeding programme was therefore undertaken to produce pea plants of agronomically acceptable character, with the rug3 mutation. Details are as follows:

1. The first crossing was undertaken early in 1993 between the five rug3rug3 SIM lines and two normal (Rug3Rug3 or ++) varieties as parents; Harrier, a Unilever bred registered variety, and Novella a leading commercial variety.
2. The crosses were carried out as a half diallel (i.e. each of the SIM lines onto each of the two varieties, without concern over which was used as the male or female).
3. The (F1) seed from the crossed flowers was harvested and F1 plants grown in insect proof glasshouses. The plants were allowed to self and the F2 seed collected during 1993.
4. The seed was sorted into wrinkled (rug3rug3-, -rr, or rug3rug3rr) (-indicates either dominant wild type or heterozygote) or round (containing at least one dominant copy of Rug3 and R). The wrinkled seed were sown in the field in spring 1994, supported by wires, and standard pedigree selection of F2 plants was done.
5. During August 1994 five F3 seed were taken from each of those plants selected from the above as having acceptable agronomic characters.
6. The F3 seed was checked for starch content. This was done by drilling a small quantity of dust from a cotyledon of each seed, and testing for starch by the addition of iodine solution. In this way the wrinkled but starchy rrRug3Rug3 lines should be rejected but the test on large numbers was imprecise and some miscategorisation probably occurred. The putative rug3rug3 lines were put into four very approximate groups (<1, <5, <10 and 10+% starch) by comparisons of the colour density with the SIM standards.
7. The remaining 765 F3 seed, all now known to be probable rug3rug3 and potentially acceptable agronomically were sown in insect proof glasshouses in October 1994.
8. When ripe, four F4 seed were taken from each of the surviving F3 plants, and sown in a large pot in the same glasshouse.
9. When ripe (May 1995) as many seed as possible up to 100 were taken from each pot and sown as a square meter F5 plot in the field.
10. The standard method of assessing maturity by tenderometer is not applicable to small plots. Hence at a date decided by the experience of the breeder, looking at and feeling the fullness of the pods, small samples were taken for the sugar analysis.
11. The samples were frozen to −18 degrees C., and sugar content was analysed by a modified Hexakinase/Glucose-6-Phosphate dehydrogenase hexose analytical technique, details of which are given below.
12. On the basis of these tests and agronomic assessment, 45 lines were selected for development, these covering a range of increased sweetness levels. The dry seed of these lines was harvested in August 1995.
13. Fifty seed of each selected line were grown up in New Zealand.
14. In March 1996 the multiplied seed (F7, but a mixture of F4 derived lines) was returned to the UK, added to the remnant F6 seed from the 1995 plots, and sown as two plots of 6.75 sq m. One plot is being harvested in July 1996 for vining and freezing, with the other being left to dry seed harvest to produce further seed to be used for larger scale trials.

The lines were checked for starch and sugar content (using the methods outlined below) at vining harvest and when dry harvested. In some cases, vining harvests were made at two maturity levels. The dry starch analysis gave the largest range of values and clearly separates the lines with and without homozygous rug3.

FIG. 9 shows clearly that in ++ or Rug3Rug3 pea varieties, sugar levels decrease with increasing tenderometer readings, while with the rug3 derived lines the decrease is much slower and high sugar levels are maintained even at high tenderometer readings.

These results can also be demonstrated by looking at the change in ratio of sucrose content:starch content with maturity. The results are shown in the following Table 5.

It can clearly be seen that in ++ or Rug3Rug3 pea varieties the ratio of sucrose content:starch content decreases much more rapidly with maturity than for the rug3 derived lines. The ratio for ++ peas at vining harvest is typically lower than for the mutant lines derived according to the invention and this difference becomes much more marked at dry seed harvest maturity. Thus, at dry seed harvest, the ratio of sucrose to starch in the rug3 lines remains higher than 0.6 in all cases whereas for the control varieties, the highest ratio recorded is only 0.26.

The results suggest that the rug3 lines are likely to exhibit increased sweetness for a given starch content at all stages of maturity compared to conventional varieties, at vining harvest and particularly at the mature dry seed stage. This has the effect of extending the range of time over which the peas can suitably be vined, thereby providing an important commercial advantage.

Analysis of the seed starch at dry seed harvest provides a convenient way of identifying those lines having the rug3 character which will give rise to plants producing peas having a high sucrose content at vining.

Autopipettes

Microcentrifuge tubes and microcentrifuge 2.b) Reagents

|  | Catalogue Number |
|---|---|
| Triethanolamine hydrochloride ($C_6H_{15}NO_3.HCl$) | Boehringer 127 426 |
| Sodium hydroxide (NaOH), 5 M and 2 M |  |
| Magnesium sulphate ($MgSO_4.7H_2O$) |  |
| NADP-$Na_2$ | Boehringer 128 058 |
| Sodium hyrdrogen carbonate ($CHO_3Na$) |  |
| ATP-$Na_2H_2$ | Sigma A-2383 |
| Hexokinase/glucose-6-phosphate DH | Boehringer 127 825 |
| Citric Acid ($C_4H_8O_7$) |  |
| Trisodium citrate ($C_4H_5Na_3O_7.2H_2O$) |  |
| Fructosidase | Boehringer 104 914 |

Preparation of Solutions 2.b.1) 2M and 5M Sodium Hydroxide Dissolve 8.0 g sodium hydroxide in water and make to 100 ml to give a 2M solution or 20.0 g sodium hydroxide in water and make to 100 ml to give a 5M solution. Cool be more making to volume.

TABLE 5

| Code | Cross | TR | Genotype | Vining 1996 % Starch | % Sucrose | Ratio Sucrose:Starch | Dry 1996 % Starch | % Sucrose | Ratio Sucrose:Starch |
|---|---|---|---|---|---|---|---|---|---|
| 1073E | Novellia × sim41 | 131 | rr | 3.9 | 5.1 | 1.31 | 22.5 | 5.3 | 0.24 |
| 1073L |  | 170 | rr | 6.1 | 3.3 | 0.54 | 22.5 | 5.3 | 0.24 |
| 1090 | Harrier × sim1 | 110 | rug3rug3 | 1.2 | 6.7 | 5.59 | 4.6 | 6.2 | 1.35 |
| 1094E | Harrier × sim1 | 127 | rug3rug3 | 0.7 | 6.3 | 9.01 | 4.4 | 2.7 | 0.61 |
| 1096E | Harrier × sim1 | 111 | rug3rug3 | 0.8 | 5.8 | 7.25 | 2.8 | 5.7 | 2.04 |
| 1096L |  | 144 | rug3rug3 | 0.7 | 6.3 | 9.01 | 2.8 | 5.7 | 2.04 |
| 1113 | Harrier × sim41 | 97 | rr | 4.3 | 4.6 | 1.07 | 20.5 | 4.3 | 0.21 |
| 1115 | Harrier × sim41 | 101 | rug3rug3 | 0.2 | 7.2 | 35.71 | 2.4 | 5.5 | 2.27 |
| 1116 | Harrier × sim41 | 116 | rug3rug3 | 0.4 | 7.3 | 18.18 | 2.5 | 6.3 | 2.50 |
| 1119 | Harrier × sim41 | 109 | rr | 3.2 | 5.5 | 1.72 | 18.4 | 4.7 | 0.26 |

Analysis of Sugars in Peas

1) Introduction

The quality of frozen peas is defined by tenderness and sweetness, which are associated since both are strongly affected by maturity. The 'tenderometer' is used commercially to gauge the maturity of peas and so suitability for harvest. Alcohol insoluble solid (AIS) content (measured either directly or by near infrared reflectance (NIR)) is used to assess tenderness in the laboratory.

The method described here is a direct, precise method of measuring the actual sugars in peas, and in practice it is only worthwhile to measure sucrose as this is by far the dominant sugar and, as the sweetest, is primarily responsible for the sweetness of the pea.

2) Equipment and Reagents 2.a) Equipment

Balance

Kinematica Microtron or similar homogeniser

Hotplate

Volumetric flasks (250 ml)

Spectrophotometer (UV/Visible, set a 340 nm)

1 cm UV type disposable cuvettes (to hold approximately 3 ml), 2.b.2) Citrate Buffer (0.32M; pH 4.6)

Dissolve 6.9 g citric acid and 9.1 g trisodium citrate in about 150 ml water, adjust the pH to 4.6 with 2M sodium hydroxide (2.b.1) and make to 200 ml with water.

2.b.3) Fructosidase

Dissolve 10 mg fructosidase in 2 ml citrate buffer (2.b.2). This is stable for at least a week in the refrigerator.

2.b.4) Triethanolamine Buffer (0.75M, pH 7.6)

Dissolve 14.0 g triethanolmine hydrochloride and 0.25 g magnesium sulphate in about 80 ml water, adjust the pH to 7.6 with 5M sodium hydroxide (2.b.1) and make to 100 ml. This buffer is stable for at least 4 weeks in the refrigerator.

2.b.5) NADP

Dissolve 60 mg NADP in 6 ml water. This is stable for at least 4 weeks in the refrigerator.

2.b.6) ATP

Dissolve 300 mg ATP and 300 mg sodium hydrogen carbonate in 6 ml water. This is stable for at least 4 weeks in the refrigerator.

2.b.7) Hexokinase/glucose6-phosphate dehydrogenase (HK/G6PDH)

Use the suspension supplied by Boehringer (Catalogue number 127 825) undiluted.

Standards

These are not required as concentrations can be calculated from absorption coefficients—see Section 6).

5) Method

5.a) Extraction

Turn the hotplate on. Weigh 25 g of fresh or frozen peas and place in a large homogeniser beaker. Add about 150 ml water and homogenise for 60 seconds at ¾ speed (Kinematica Microtron). Pour the homogenate into a 250 ml beaker, rinse the homogeniser beaker a couple of times and add the washings to the homogenate. Bring the homogenate to the boil on a hotplate to kill all the enzymes, extract the sugars and coagulate the proteins. Then cool the homogenate in a sink of water and pour into a 250 ml volumetric flask. Rinse the beaker until it is clean, adding the rinsings to the volumetric flask. Make the flask to volume.

Allow the sediment in the volumetric flask to settle for about 30 minutes and take off some of the supernatant. Place this in microcentrifuge tube(s) and centrifuge at 10,000 rpm for 5 minutes. To measure sucrose a further dilution is required. Take 2 ml or 5 ml of the spun supernatant and make to 10 ml or 25 ml respectively with water.

5.b) Measurement of Sugar

Turn on the spectrophotometer and set the wavelength to 340 nm with both the deuterium and visible lamps switched on.

Pipette the following solutions as detailed in Table 6 into a disposable UV cuvette and read the OD against the water blank.

The sample solution must not contain more that 150 μg sucrose per cuvette. If this is the case make a further dilution.

TABLE 6

Volumes of Solutions for Each Assay

| Pipette into cuvettes (ml) | Blank Sample ml | Glucose Analysis ml | Sucrose Analysis ml |
|---|---|---|---|
| Citrate Buffer (2.b.2) | 0.20 | — | 0.20 |
| Sample | — | 0.10 | 0.10 |
| Fructosidase (2.b.3) | 0.02 | — | 0.02 |
| Mix, keep at room temperature for 15 minutes. The add: | | | |
| Trieth buffer (2.b.4) | 1.00 | 1.00 | 1.00 |
| Water | 1.00 | 1.12 | 0.90 |
| NADP (2.b.4) | 0.10 | 0.10 | 0.10 |
| ATP (2.b.6) | 0.10 | 0.10 | 0.10 |
| Mix, read absorbances after about 3 minutes = A1. START by adding: | | | |
| HK/G6PDH (2.b.7) | 0.02 | 0.02 | 0.02 |

Mix wait for the completion of the reaction (10 to 15 minutes) and then read the absorbances = A2.
If the reaction has not stopped continue to read the absorbances at 15 minute intervals until the reading is constant. The blank should be stable.

| Total volume | 2.44 | 2.44 | 2.44 |

6) Results

Sucrose $$\frac{2.44 \times 342.3 \times \text{absorbance} (A2 - A1)}{6.3 \times 0.1 \times 1000} = 1.326 \times \text{absorbance g/l}$$

where:
  2.44=total volume
  342.30=molecular weight of sucrose
  6.3=absorption coefficient of NADPH at 340 nm
  0.1=sample volume
  25 g peas are made to 250 ml, 2 ml of homogenate are made to 10 ml=10×5=50×dilution, or the equivalent of extracting 25 g of peas in 1250 ml.
  So 1.326×Absorbance×50=Sucrose per g of peals, fresh weight.

Glucose $$\frac{2.44 \times 180.16 \times \text{absorbance} (A2 - A1)}{6.3 \times 0.1 \times 1000} = 0.698 \times \text{absorbance g/l}$$

where:
  2.44=total volume
  180.16=molecular weight of glucose
  6.3=absorption coefficient of NADph at 340 nm
  0.1=sample volume
  ×50=mg per g of peas, fresh weight.
  So 0.698×Absorbance×50=glucose per g of peas, fresh weight.

NOTE: The glucose concentration is low and need not usually be measured. However, to be strictly correct, the sucrose measurement will be sucrose + glucose and so to get a true sucrose measurement, measure both and subtract glucose from sucrose.

8) Summary

Homogenise 25 g peas in 150 ml water for 60 seconds Boil the homogenate
Make to 250 ml
Centrifuge and dilute the supernatant×5
Add sample buffer and fructosidase to cuvette, mix and incubate for 15 minutes
Add buffer, water, NADP and ATP to cuvette, mix and read absorbance after 3 minutes=A1
Add HK/G6PDH, mix and read absorbance after completion of reaction (10 to 15 minutes)=A2
Calculate % sucrose and % glucose Cloning of the Pea PGM(R) cDNA Gene and Genetic Segregation Analysis A. Materials and Methods 1. Preparation of cDNA Library RNA was isolated from immature pea embryos (*Pisum sativum* Var. Novella) weighing 200 mg. Isolation was carried out using the Quickprep mRNA Purification Kit (Pharmacia). First and second strand cDNA was synthesised using the Superscript II cloning kit (GIBCO-BRL) with first strand cDNA being primed by oligo(dT). cDNA ends were blunt-end ligated to EcoRI adapters and excess adapters removed through Sephacry1–300 columns (Pharmacia). The inserts were ligated into a Lambda ZAP II vector and packaged using the Gigapack III packaging extracts (both Stratagene). A portion of the library was plated, 24,000 pfu, with an average insert size of 1.5 Kbp and largest PCR amplifiable insert of 3 Kbp. Filters (Hybond N+) were lifted from plates and uv-fixed prior to hybridisation.

2. Amplification of PGM Gene Fragment

Degenerate primers (5'-ACIGCIWSICAYAAYCC (SEQ ID No. 1) & 5'-CKRTCICCRTCICCRTCRAAIGC (SEQ ID No. 2)) were synthesised, based on regions of conserved amino acid sequence in known PGM genes from *E. coli*, yeast, rabbit, rat and human. PCR amplification of cDNA (Novella) using standard conditions (25 µl reaction mixture containing; 0.2 mM DNTP, 0. 3 µM each oligonucleotide primer, 10 mM Tris pH 8.3, 50 mM KCl, 1.5 mM $MgCl_2$ and 0.5 units Taq DNA Polymerase, Advanced Biotechnologies) and a standard PCR cycle with anneal temperature of 44° (Phillips et al, Theor Appl Gene 88:845–851, 1994) yielded a fragment of the expected size (500 bp). This was cloned using the pT7Blue T vector kit (Novagen) and end-sequenced. This confirmed considerable homology with known PGM sequences.

3. Library Screening

The PCR product (above) was labelled with $^{32}P$ (Feinberg & Vogelstein, Anal Biochem 132:6–13, 1983) and hybridised to library filters at 65° overnight. The filters were washed at high stringency (0.1×SSC at 65°) and exposed to X-ray film at −70°. Positive plaques were purified and PCR amplified to ascertain insert size.

4. Genetic Segregation Analysis

Segregating populations were constructed through crossing the conventional Rug3 vining cultivar (Harrier) with the rug3 Sim line 43 and generation of F2 (population A) and F4 (population B) lines. Plants were phenotyped through a combination of visual inspection of their seed (Rug3= wrinkled, rug3 -super-wrinkled) and iodine staining of leaf tissue. DNA from segregating populations was isolated (Dellaporta et al, Plant Mol Biol Rep. 1:19–21, 1983), restricted with EcoRI and electrophoresed through it 1% agarose prior to capillary blotting (Sambrook et al, 1989). The insert from the longest cDNA library clone was labelled with $^{32}p$ and used as a probe.

1. Cloning of the Pea Plastidial Phosphoglucomutase cDNA Gene

A DNA sequence comparison was made between previously reported PGM genes from the species described below. Two regions of high conservation were identified and used to design degenerate oligonucleotide PCR primers. Amplification of pea cDNA resulted in generation of a DNA fragment of the expected size. A cDNA library was constructed and this PCR product used as a probe. A total of 38 positive plaques were identified. The largest insert size was 2.2 kb, corresponding to the expected coding capacity predicted from other cloned PGM genes and also the size of the mRNA transcript on Northerns. The DNA sequence of this clone was determined (FIG. 1). The amino acid sequence of the largest open reading frame minus the putative transit peptide domain was compared with that of other cloned PGM genes using the standard computer program DNAStar (DNAStar Inc, Madison, USA) and the results shown in table 7. This shows considerable regions of homology throughout the gene. Highest homology is found with the sequence from the ice plant (*Mesembryantlemum crystallinum*), followed by that from *Agrobacterium tumefaciens*, then mammalian and yeast genes and finally to *Escherichia coli* and Xanthomonas. However the Pea cDNA reported here has an extension of approximately 65 amino acids at the N terminal end, suggesting a role as a transit peptide for import into plastids. Supportive evidence for this role comes from the high content of serine residues found in many such transit peptides.

TABLE 7

| Percent Divergence | Percent Similarity | | | | | | | | | | |
|---|---|---|---|---|---|---|---|---|---|---|---|
| | 1 | 2 | 3 | 4 | 5 | 6 | 7 | 8 | 9 | | |
| 1 | | 61.0 | 57.0 | 56.0 | 56.0 | 56.0 | 46.0 | 17.0 | 16.0 | 1 | Pea |
| 2 | 15.2 | | 55.0 | 57.0 | 57.0 | 57.0 | 46.0 | 17.0 | 16.0 | 2 | Iceplant |
| 3 | 16.3 | 19.8 | | 55.0 | 55.0 | 55.0 | 50.0 | 20.0 | 17.0 | 3 | Agrobacterium tumefaciens |
| 4 | 18.2 | 19.4 | 17.5 | | 90.0 | 96.0 | 51.0 | 18.0 | 18.0 | 4 | Human |
| 5 | 19.0 | 19.9 | 17.9 | 3.1 | | 91.0 | 51.0 | 17.0 | 17.0 | 5 | Rabbit |
| 6 | 18.0 | 19.5 | 17.5 | 1.2 | 3.3 | | 51.0 | 17.0 | 17.0 | 6 | Rat |
| 7 | 23.9 | 24.5 | 22.7 | 20.8 | 21.5 | 20.8 | | 16.0 | 14.0 | 7 | Yeast |
| 8 | 35.4 | 36.1 | 33.2 | 35.2 | 35.9 | 35.1 | 36.8 | | 58.0 | 8 | *E Coli* |
| 9 | 34.8 | 36.1 | 33.2 | 34.3 | 35.0 | 34.5 | 35.7 | 12.0 | | 9 | Xanthamonas |
| | 1 | 2 | 3 | 4 | 5 | 6 | 7 | 8 | 9 | | |

2. Genetic Segregation Analysis

Populations segregating for the rug 3 "super-wrinkled" phenotype were tested for linkage between the pPGM gene and the rug3 phenotype. Table 8 shows the results for two such populations.

TABLE 8

| | Genotype RFLP alleles at pPGM locus. | | | |
|---|---|---|---|---|
| | Population A | | Population B | |
| Phenotype | RugRug/ Rugrug | rugrug | RugRug/ Rugrug | rugrug |
| Wild type | 77 | 0 | 33 | 0 |
| rug3 "super-wrinkled" | 0 | 21 | 0 | 9 |

In population A, the segregation of wild type and rug3 "super-wrinkled" plants did not differ significantly from a 3:1 segregation ratio as expected for a recessive gene inherited in a classically Mendelian fashion. In all cases the ruq3 plants were homozygous for the RFLP allele derived from the rug3 parental plant. A similar observation was found in population B.

This data demonstrates that the rug3 mutation maps very closely to, or on top of, the pPGM gene.

What is claimed is:

1. A process for extending harvest window of a pea plant and/or increasing sucrose content of a pea plant, or part thereof, comprising reducing plastidial phosphoglucomutase (PGM(p)) activity in said pea plant, or part thereof.

2. The process of claim 1, wherein the PGM(p) has the amino acid sequence of SEQ ID NO:4 or an amino acid sequence with at least 60% sequence homology to SEQ ID NO:4 and which has PGM(p) activity.

3. The process of claim 1 or 2, wherein the process comprises introducing into the plant, or part thereof, a mutation into the polynucleotide sequence encoding the amino acid sequence of SEQ ID NO:4 or into a polynucleotide sequence encoding an amino acid sequence with at least 60% sequence homology to SEQ ID NO:4 and which has PGM(p) activity.

4. The process of claim 1 or 2, wherein the process comprises introducing into the genome of the plant, or part thereof, in a sense or antisense orientation, a polynucleotide sequence of SEQ ID NO: 3 or a polynucleotide sequence with at least 60% sequence homology to SEQ ID NO:3, wherein the homologous polynucleotide sequence inhibits PGM(p) activity.

5. An isolated polynucleotide sequence encoding the amino acid sequence of SEQ ID NO:4 or encoding an amino acid sequence with at least 95% sequence homology with the amino acid sequence of SEQ ID NO:4.

6. A vector comprising the polynucleotide of claim 5.

* * * * *